(12) United States Patent
Neta et al.

(10) Patent No.: US 10,137,242 B2
(45) Date of Patent: *Nov. 27, 2018

(54) FLUID DISPENSING DEVICE WITH A FLOW DETECTOR

(71) Applicant: Roche Diabetes Care, Inc., Indianapolis, IN (US)

(72) Inventors: Avraham Neta, Gilon (IL); Konstantin Tsypko, Carmiel (IL); Nikolay Tsypko, Natzaret-Illit (IL); Ofer Yodfat, Modi'in (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 219 days.

This patent is subject to a terminal disclaimer.

(21) Appl. No.: 14/950,661

(22) Filed: Nov. 24, 2015

(65) Prior Publication Data
US 2016/0074577 A1    Mar. 17, 2016

Related U.S. Application Data

(63) Continuation of application No. 13/872,938, filed on Apr. 29, 2013, now Pat. No. 9,227,010, which is a
(Continued)

(51) Int. Cl.
*A61M 5/142* (2006.01)
*A61M 5/168* (2006.01)
(Continued)

(52) U.S. Cl.
CPC .... *A61M 5/14244* (2013.01); *A61M 5/14248* (2013.01); *A61M 5/16831* (2013.01);
(Continued)

(58) Field of Classification Search
CPC ......... A61M 2005/14268; A61M 2005/16863; A61M 2205/3334; A61M 2205/3368;
(Continued)

(56) References Cited

U.S. PATENT DOCUMENTS 4,255,968 A * 3/1981 Harpster ............... G01F 1/6847
    73/204.18
7,935,104 B2 * 5/2011 Yodfat ................ A61M 5/1413
    604/890.1
(Continued)

FOREIGN PATENT DOCUMENTS

EP    1177802 A1    2/2002
WO    2009125398 A2   10/2009

OTHER PUBLICATIONS

Hermansen, K., et al., "Efficacy and safety of the dipeptidyl peptidase-4 inhibitor, sitagliptin, in patients with type 2 diabetes mellitus inadequately controlled on glimepiride alone or on glimepiride and metformin", Diabetes Obes Metab. Sep. 2007; 9(5); 733-745; Epub Jun. 26, 2007; Abstract.

Hoogma, R., et al., Comparison of the effects of continuous subcutaneous insulin infusion (CSII) and NPH-based multiple daily insulin injections (MDI) on glycaemic control and quality of life: results of the 5-nations trial, 2005, Diabetes UK, Diabetic Medicine, 23, 141-147.

*Primary Examiner* — Quynh-Nhu H Vu
(74) *Attorney, Agent, or Firm* — Dinsmore & Shohl LLP

(57) ABSTRACT

A portable therapeutic fluid delivery device with a flow detector comprising a heating element and two temperature sensors is presented. Upon activation of the heating element, a flow condition of the fluid inside the delivery tube is determined based on a signal provided by the temperature sensors. A temperature gradient within the therapeutic fluid is detected. The determined flow condition can be one of: air bubbles within the delivery tube, occlusion within the delivery tube, or leakage within the delivery tube. The device can have two parts, for example, a reusable part and a disposable part. Upon pairing of these parts, the heating element and the temperature sensors touch the delivery tube.

26 Claims, 27 Drawing Sheets

Related U.S. Application Data continuation of application No. PCT/EP2011/005491, filed on Oct. 29, 2011.

(60) Provisional application No. 61/408,941, filed on Nov. 1, 2010.

(51) Int. Cl.
   *A61M 5/145* (2006.01)
   *A61M 5/36* (2006.01)

(52) U.S. Cl.
   CPC ....... *A61M 5/16886* (2013.01); *A61M 5/1452* (2013.01); *A61M 5/365* (2013.01); *A61M 2005/14268* (2013.01); *A61M 2005/16863* (2013.01); *A61M 2205/3334* (2013.01); *A61M 2205/3368* (2013.01)

(58) Field of Classification Search
   CPC .......... A61M 5/14244; A61M 5/14248; A61M 5/1452; A61M 5/16831; A61M 5/16886; A61M 5/365

See application file for complete search history.

(56) References Cited

U.S. PATENT DOCUMENTS

| | | | |
|---|---|---|---|
| 8,313,468 B2* | 11/2012 | Geipel | A61M 5/158 604/151 |
| 9,227,010 B2* | 1/2016 | Neta | A61M 5/14248 |
| 2003/0167036 A1* | 9/2003 | Flaherty | A61M 5/14248 604/67 |
| 2004/0000196 A1 | 1/2004 | Kleinlogel et al. | |
| 2005/0204811 A1 | 9/2005 | Neff | |
| 2007/0106218 A1 | 5/2007 | Yodfat et al. | |
| 2008/0077081 A1 | 3/2008 | Mounce et al. | |
| 2008/0154187 A1 | 6/2008 | Krulevitch et al. | |
| 2008/0257412 A1* | 10/2008 | Gordon | A61M 5/16877 137/8 |
| 2010/0172816 A1 | 7/2010 | Mayer et al. | |
| 2012/0210781 A1* | 8/2012 | Klee | G01F 1/688 73/204.23 |

* cited by examiner

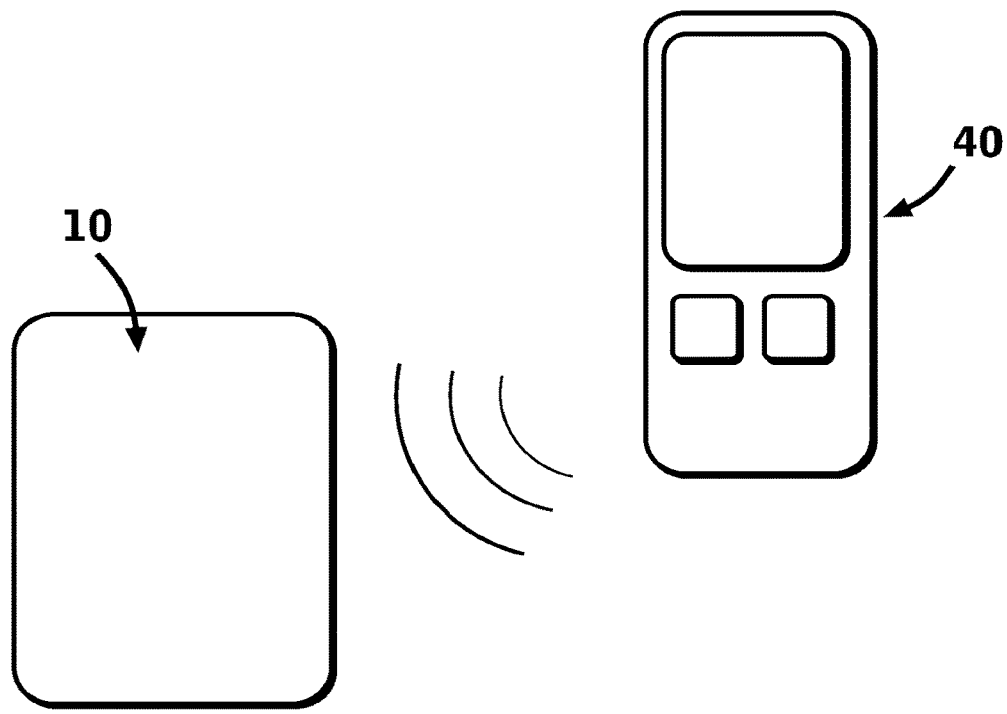
Fig. 1a
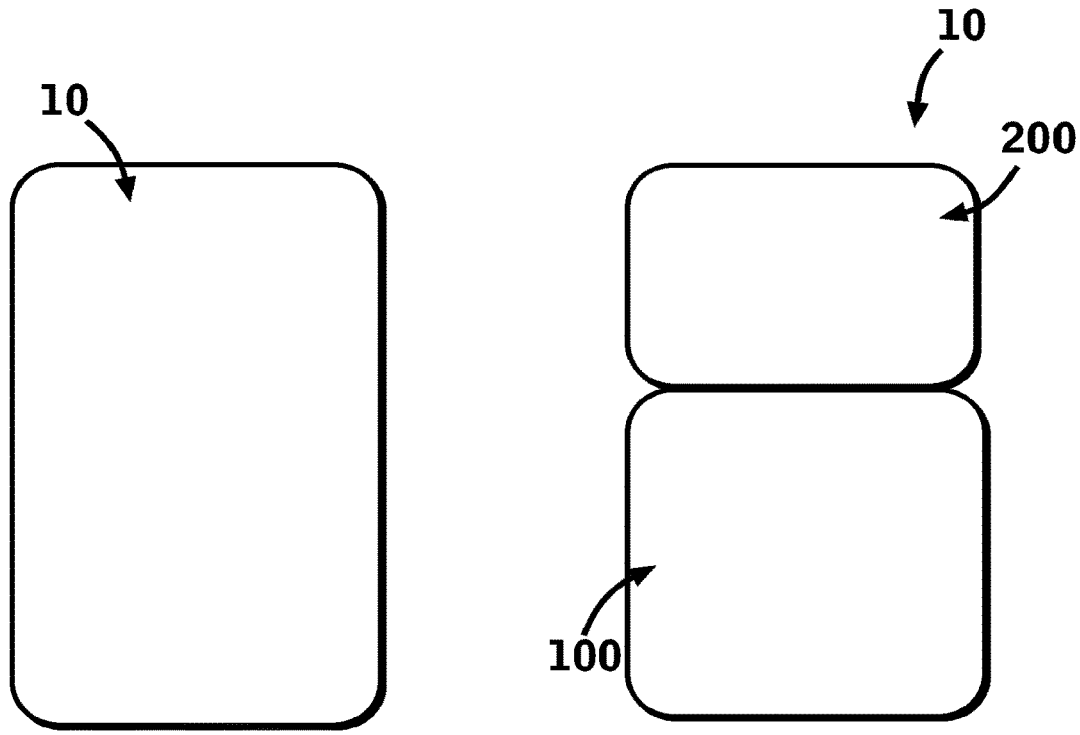
Fig. 1b
Fig. 1c

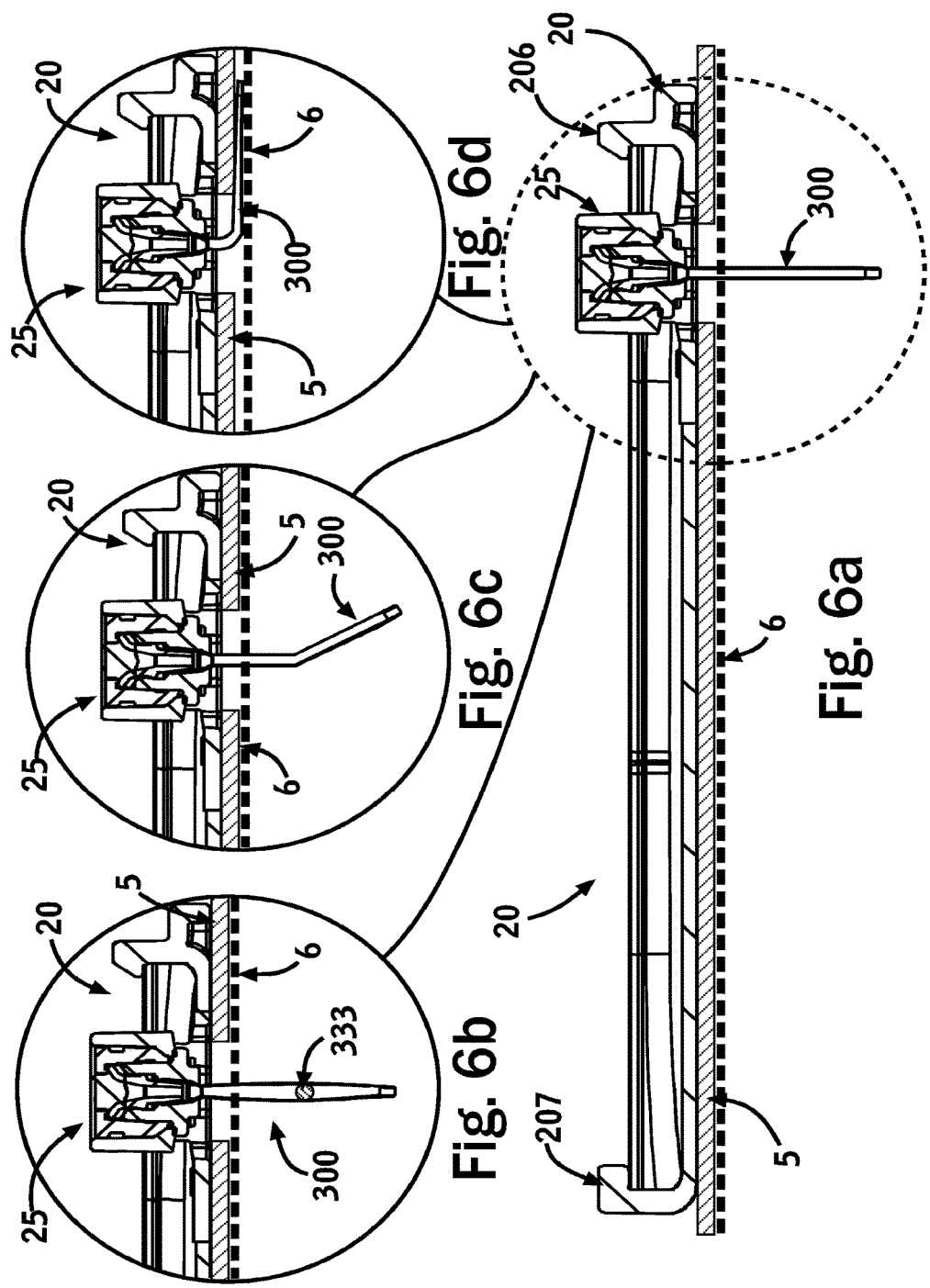

| | DETECTION | NO FLOW | MISSING PULSE | END OF RESERVOIR |
|---|---|---|---|---|
| 1 | OCCLUSION | ✓ | ✗ | ✗ |
| 2 | AIR BUBBLES | ✓ | ✗ | ✗ |
| 3 | NO INSULIN | ✓ | ✓ | ✓ |
| 4 | MOTOR ERROR | ✓ | ✓ | ✗ |

Fig. 12

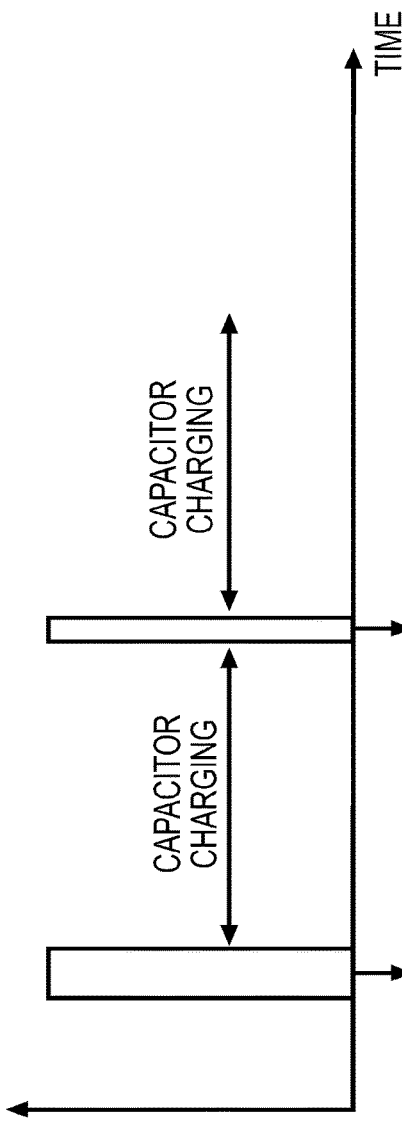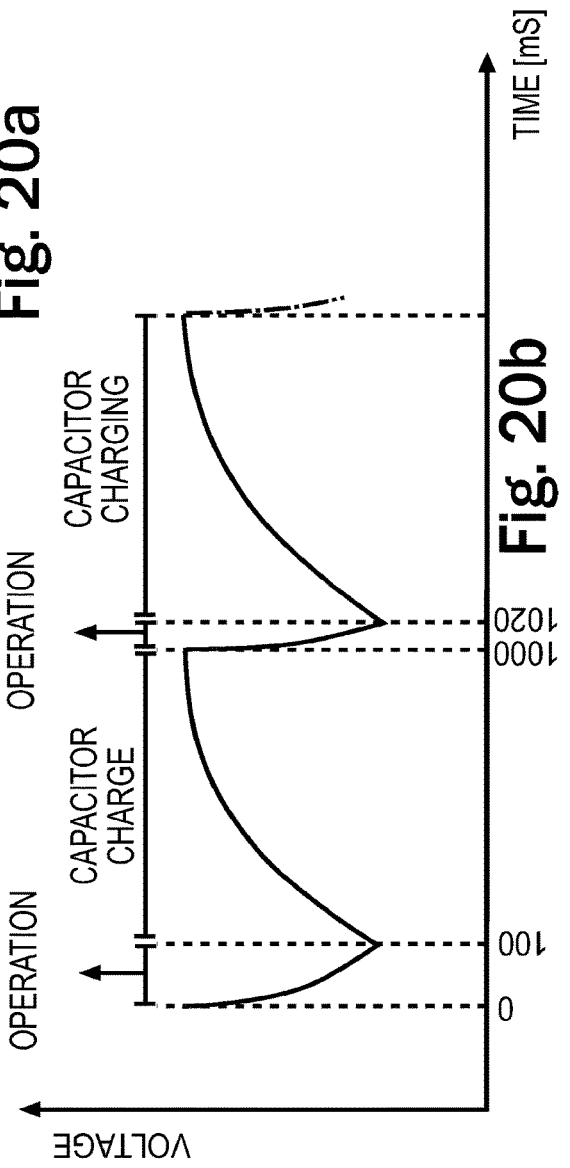

FLUID DISPENSING DEVICE WITH A FLOW DETECTOR

CROSS-REFERENCE TO RELATED APPLICATIONS

This application is a continuation of U.S. patent application Ser. No. 13/872,938, filed on Apr. 29, 2013, which is a continuation of PCT/EP2011/005491, filed Oct. 29, 2011, which is based on and claims priority to U.S. Provisional application 61/408,941, filed Nov. 1, 2010, which is hereby incorporated by reference.

BACKGROUND

The present disclosure generally relates to systems, devices, and methods for dispensing of therapeutic fluid and, in particular, to a device with a flow sensor or flow detector as well as to methods that makes use of such sensors or flow detectors.

Medical treatment of several illnesses requires continuous or periodic drug infusion into various body compartments through subcutaneous and intra-venous injections. Diabetes mellitus (DM) patients, for example, require the administration of varying amounts of insulin throughout the day to control the patients' glucose levels. In recent years, ambulatory portable Continuous Subcutaneous Insulin Infusion (hereinafter "CSII") pumps have emerged as a superior alternative to the use of multiple daily injections (hereinafter "MDI") of insulin, initially for Type 1 diabetes patients, and subsequently for Type 2 diabetes patients. These pumps, which deliver insulin at a continuous or periodic basal rate, as well as in bolus volumes, were developed to free patients from repeated self-administered injections, and to allow them to maintain a near-normal daily routine. Both basal and bolus volumes have to be delivered in precise doses, based on individual prescription, because an overdose or underdose of insulin could be fatal. In the context of the present disclosure, "continuous delivery" includes a quasi-continuous delivery where small drug amounts are delivered in time intervals of typically some minutes, resulting in the pharmacological effect being substantially identical to a steady continuous delivery.

Insulin administration of basal and bolus doses is dependent on body glucose levels. Diabetes patients generally monitor their glucose levels and adjust insulin dosing accordingly. Glucose levels may be monitored by using blood-sensitive test strips (obtaining a blood sample through finger pricking), or by using removable insertable subcutaneous sensors. Insulin pumps can receive glucose measurements from glucose monitors either manually (inputting numbers with a keypad) or by automatically communicating (e.g., wirelessly) glucose readings from a remote glucose monitor.

Some portable infusion pumps include "pager-like" devices, where such a pager-like device includes a reservoir contained within the device housing. These devices are provided with a tube for delivering insulin from the pump which is, for example, attached to a patient's belt to a remote insertion site. The tubing length is in a range of typically 30 cm to 1.5 m. Pumping is achieved, for example, by linear movement of a piston/plunger within a reservoir in a syringe-like way, forcing fluid to be expelled from the reservoir to the outlet port. A processor-controlled motor and gear arrangement provides controlled rotational motion that is converted to linear movement by a rotation of a nut over a plunger rod drive screw.

Both basal and bolus volumes delivered in these "pager-like" devices are typically controlled via a set of buttons provided on the device. A user interface screen is typically provided on the device housing to provide the user with information about fluid delivery status, to program flow delivery, and to provide alerts and alarms. These devices represent a significant improvement over a regiment based on multiple daily injections, but, nevertheless, suffer from several drawbacks, among which are the large size and weight of such devices, their long delivery tubing, and lack of discreetness.

To avoid the consequences of comparatively long tubing for connecting pump and cannula, a new concept, an alternative architecture was proposed. This architecture is based on a remote controlled skin adherable device with a housing having a bottom surface adapted for contact with the patient's skin, a reservoir disposed within the housing, and an injection needle in communication with the reservoir. In these devices, the user interface is provided as a separate remote control unit that contains operating buttons and a screen to provide fluid delivery status, to program flow delivery, to provide alerts and alarms, and the like. Corresponding devices still have several limitations, including their heavy and bulky configuration, and the relative high cost resulting from their use due to the fact that the devices have to be replaced after several days (e.g., 2-3 days). Another drawback associated with this type of skin adherable devices relates to the required remote control. The user is generally totally dependent on the remote control unit and cannot initiate bolus delivery or operate the device if the remote control unit is not at hand, is lost or malfunctions.

A general limitation of current insulin pump devices is their lack of flow feedback. There is typically no monitoring or supervision of insulin flow within the delivery path after insulin is expelled from the reservoir outlet port by, for example, a plunger/piston linear movement, resulting in typical defects and/or hazardous situations, such as occlusions, air bubbles, or leakage being detected only with a large time delay of typically several hours. In dependence of the specific design, some of these situations may not be detected at all by the device.

In addition, the required insulin volume (dose) administration is achieved by programmed timing of motor operation, and counting motor or gear revolution with an encoder. This revolution is converted to a proportional linear movement of the drive screw and plunger (motor gear revolution reduction ratio is a fixed number). The distance of plunger/piston linear movement may be derived from the motor and gear number of revolutions and pitch of the drive screw and is proportional to the administered volume according to the drug reservoir cross section. Delivery accuracy is accordingly dependent on the precision of gears' cogwheels and drive screw pitch accuracies as well as the accuracy of the reservoir cross section. Slight deviations of those influence factors, resulting, e.g. from manufacturing and/or assembly tolerances as well as from operation wear-and-tear can affect the precision of linear movement, and consequently affect delivery accuracy. Furthermore, failures of the motor revolution counter (encoder) can cause uncontrolled motor operation, and consequently cause over- or under insulin delivery. In some cases, a long time delay for detecting defects or hazards or an over-or under delivery may result in serious medical complications, both short term and/or long/term.

A known problem of current insulin pumps both of the skin securable or pager type is the higher occurrence of severe high blood sugar events and diabetes ketoacidosis (DKA). DKA is a potentially life-threatening complication in patients with diabetes mellitus and results from an absolute or relative shortage of insulin (under or no insulin delivery). In response to glucose deprivation the body switches to burning fatty acids and producing acidic ketone bodies that cause most of the symptoms and complications. The main reasons for insulin under-delivery and consequently DKA in diabetes pump users are the occurrence of occlusion in the insulin path, air bubbles, and leakage. Occlusions occur when something blocks the infusion line. The causes can be manifold: a kink in the line, insulin crystallization, deposits of fibrin, blood clot, lipid residues, and the like. Insulin path occlusion can be detected in current pumps by monitoring pressure or torque readings from part of the insulin pump drive train (pulses generated in the processor to operate the motor). The patient is notified with an alarm when any reading exceeds a predetermined threshold.

Another implementation for detecting an occlusion in a fluid delivery tube is based on a detection of tube's radial expansion. The expansion is caused by an elevation of an upstream pressure that is caused by a downstream occlusion. Various components may be used to measure tube radial expansion, including a magnet sensitive element, resilient diaphragm, and others. In one example, an alarm is triggered by a pair of pressure sensors located at two different places along the insulin flow passage in the pump. In another example, an occlusion detector detects alteration in the shape of the insulin delivery tube.

In some of these occlusion detectors there, is a long lag time between the occurrence of occlusion and the detection of the occlusion (and alarm activation). Pressure buildup within the delivery path is usually very slow at low delivery rates typically used in insulin pump. For example, in one type of a commercial pump, occlusion is triggered by an average of 2.77 units of "missed insulin" with a typical time before alarm at a basal delivery rate of 0.05 U/h being 59.2 hours. Thus, from a practical perspective, this occlusion detector may not be able to prevent severe hyperglycemia and/or DKA, which usually occur only a few hours (e.g., 3-4 hours) after occurrence of occlusion.

Furthermore, existences of air bubbles in any medication infusion tubing can cause under-delivery. In portable ambulatory insulin pumps, especially at low programmed delivery rates, air bubbles can result in cessation of insulin administration for many hours and may consequently result in hyperglycemia and/or DKA. Tubing in currently existing insulin pager pumps extend from the pump housing to the user body insertion site, thus any air bubbles detector to detect bubbles in tubing needs to be external to the pump housing or somehow connected to the delivery tube. Typical current skin adherable insulin dispensing devices have no air bubbles detectors.

Leakage from the insulin path is another cause for insulin under delivery or completely missing delivery. Leakage can be related to cannula dislodgement from the subcutaneous insertion site. Because skin surface is usually covered by adhesive tape the user cannot see the leaking cannula. Other causes for leakage are related to leakage from the insulin delivery tube or tube connectors. Typical current insulin pumps do not have leakage detectors.

To address those drawbacks, a pump with at least two subcutaneous electrodes monitors a temporary conductivity variation in the subcutaneous tissue upon drug administration, thus allowing monitoring the correct execution of each administration.

Therefore, there is a need for a skin adherable infusion device that is inexpensive and that extends patient customization.

SUMMARY

According to the present disclosure, a system and method for determining a flow condition of therapeutic fluid in a two-part portable fluid delivery device is presented. A first reusable part comprising a rotary motor and a flow detector is provided. The flow detector comprises at least one heating element and at least two temperature sensors. A second disposable part comprising a reservoir, an exit port, and a delivery tube that communicates between reservoir and exit port is provided. The first reusable part and the second disposable part are paired such that the flow detector touches the delivery tube. The heating element, the motor and the as least two temperature sensors are operated sequentially. The flow condition is determined based on a signal provided by the at least two temperature sensors.

Accordingly, it is a feature of the embodiments of the present disclosure to provide a skin adherable infusion device that is inexpensive and that extends patient customization. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIGS. 1a-c illustrate a schematic diagram of an example therapeutic and monitoring system that includes a skin securable patch unit and a remote control unit according to an embodiment of the present disclosure.

FIGS. 6a-d illustrate cross sectional views of an example cradle and adhesive after insertion of a tip through a well and into the body according to an embodiment of the present disclosure.

FIGS. 7a-b illustrate an example disposable part that includes a reservoir filled with therapeutic fluid according to an embodiment of the present disclosure.

FIG. 12 illustrates a decision table based summarizing the various conditions causing no-flow according to an embodiment of the present disclosure.

FIGS. 20a-b illustrate graphs showing the sequence of heating element and motor activation according to an embodiment of the present disclosure.

DETAILED DESCRIPTION

Figure 2A:
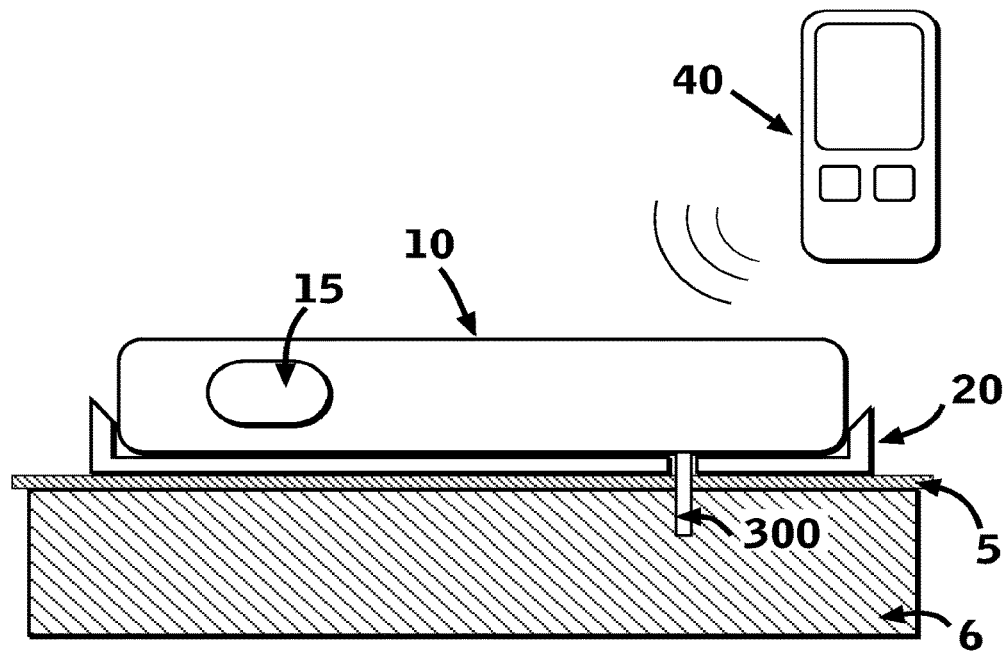
FIGS. 2a-b illustrates an example skin securable patch unit connected to a skin adherable cradle according to an embodiment of the present disclosure. The patch unit may be disconnected from and reconnected to a cradle unit and can be comprised of one part (2a) or two parts (2b).

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The systems, devices and methods as disclosed herein may be particularly useful in the context of Diabetes therapy via Continuous Subcutaneous Insulin Infusion (CSII) with the therapeutic fluid being a liquid insulin formulation. However, the systems, devices and methods described herein are not limited to delivering insulin but, rather, apply to delivering any other drug and to, optionally, concomitantly monitor analyte. When used in the following description, the term "analyte" can mean any solute composed of specific molecules dissolved in an aqueous medium.

A type of skin adherable infusion devices to alleviate cost issues and to extend patient customization is presented. Such a device generally can include a remote control unit and a skin securable device/patch unit that may comprise two parts: a reusable part comprising a driving mechanism, electronics, and other relatively expensive components and a disposable part comprising a reservoir, and, in some embodiments, a power source (e.g., batteries). The disposable part may also include other relatively inexpensive components.

The term "disposable" can indicate that the part can be used for a limited application time which can be in a typical range of some days up to e.g. two weeks. Such a disposable part does not include any component that requires or generally allows maintenance or repair. The concept underlying this device can provide a cost-effective, skin securable infusion device, and can enable diverse usage through use of various reservoir sizes, various needle and cannula types, and the like.

Such a pump can be remotely controlled or can be operated by dedicated control buttons located on the patch housing. For such devices, the user can deliver a desired bolus dose by repeated pressing the control buttons.

The skin adherable insulin pumps may include a continuous glucose monitor including a glucose sensing mechanism. The subcutaneous cannula includes a glucose sensing probe and glucose readings can be displayed on a remote control screen.

Such fluid flow detectors can comprise a heating element and two temperature sensors. Upon activation of the heating element, a flow condition of the fluid inside the delivery tube can be determined based on a signal provided by the temperature sensors. A temperature gradient within the therapeutic fluid can be detected. The determined flow condition can be one of: air bubbles within the delivery tube, occlusion within the delivery tube, or leakage within the delivery tube or combinations thereof. In some embodiments, the therapeutic fluid can be incompressible (i.e. not compressible or with negligible compressibility). In this case, the flow condition assessed in the delivery tube can also be true for (is the same than) the flow condition in the fluid delivery path situated downstream the delivery tube (any delivery circuit situated "after" the delivery tube when following the flow direction). For example, if the condition is "no flow" in the delivery tube, it can mean that there is "no flow" in the cannula connected after the exit port of the delivery tube. In other words, the determined flow condition associated with the delivery tube can also be associated with downstream path elements such as the exit port or the cannula.

In one embodiment, a particular portable therapeutic fluid delivery can be provided in two parts, for example, a reusable and a disposable part. Upon the pairing of these parts, the heating element and the temperature sensors can touch the delivery tube. The first part can be a reusable part comprising a driving mechanism, the driving mechanism including a rotary motor and at least one gear, and a flow detector. The flow detector can comprise the at least one heating element, at least two temperature sensors, and a processor. The second part can be the disposable part comprising a reservoir, an exit port, and a delivery tube communicating between reservoir and exit port.

Of course, the distribution of components over the two parts can be changed and/or evolve over time according to different device designs. Generally, the reusable part comprises the most expensive components and the disposable part the cheapest ones. But various considerations can modify this choice, having no technical consequences. For example, the battery or energy source originally thought as disposable can become rechargeable and can be included in the reusable part. Other grounds or considerations can lead to modify this distribution of elements or components over the two parts: business and economic considerations, environmental motivations, manufacturing reasons, user convenience, and the like. The principle remains that upon pairing of the two (or more) parts, the heating/sensing system can be enabled and when operated, can be enabled to assess the fluid flow condition. The disposable part and the reusable part can be designed such that upon pairing of the reusable part with the disposable part, the at least one heating element and the at least two temperature sensors can touch the delivery tube. The processor, upon activation of the heating element, can detected a flow condition of the therapeutic fluid inside the delivery tube based on a signal provided by the at least two temperature sensors.

The proposed architecture can allow the more complex components of the device and in particular of the flow detector, to be used with a number of disposable parts in sequence, thus reducing the device and therapy costs as compared to where the complete flow detector or the device as while is discarded after some days of application.

In some embodiments, the at least one heating element and the at least two temperature sensors can be arranged on a printed circuit board (PCB) of the reusable part.

In some embodiments, the delivery device can detect a temperature gradient within the therapeutic fluid and can determine the flow condition based on the temperature gradient. The temperature gradient may be determined as temperature difference measured by the at least two temperature sensors, e.g. an upstream temperature sensor that is upstream of the at least heating element and a downstream temperature sensor that is downstream of the at least one heating element. Such a temperature difference can serve as estimate for the temperature gradient inside the fluid.

In some embodiments, the flow condition can comprise at least one of: air bubbles within the delivery tube, an occlusion within the delivery tube, a leakage within the delivery tube or combinations thereof. Those flow conditions can reflect defect or other hazardous situations.

In some embodiments, the delivery device can alarm the patient regarding conditions of one or more of: occlusion, air bubbles, and leakage in the delivery tube.

In some embodiments, the delivery device can comprise a skin securable drug dispensing unit comprising the reusable part and the disposable part.

In some embodiments, the delivery device can be remotely controlled.

In some embodiments, the drug dispensing unit can include buttons and the delivery device can be operated manually by operating the buttons.

In some embodiments, the drug dispensing unit can disconnect from and reconnected to a skin adherable cradle unit.

In some embodiments, the disposable part can include an energy supply.

In some embodiments, the delivery device can include a handheld remote control unit comprising an integrated blood glucose monitor.

In some embodiments, the drug dispensing unit can include a blood glucose sensing unit.

In some embodiments with a blood glucose sensing unit, the device can include one subcutaneous insertable tip that serves both as therapeutic fluid cannula and sensing probe.

In some embodiments, the motor can be a stepper motor. Alternatively, the motor may, e.g., be a standard DC motor or a brushless DC motor.

In some embodiments that include a stepper motor, the delivery device can include a pulse generator coupled to the stepper motor to operate the stepper motor. The delivery device can further detect an occlusion by detecting a mismatch between pulses supplied to the motor and motor operation. Motor operation may be monitored and determined via a rotatory encoder or revolution counter.

In some embodiments, the delivery device can cause power to be delivered to the at least one heating element; can cause power delivery to the at least one heating element to be suspended, and can cause power to be delivered to the motor to begin motor operation subsequent to the suspension of power delivery to the at least one heating element. The power delivered to the motor can cause the heated therapeutic fluid to flow in the delivery tube.

In some embodiments, the delivery device can include a capacitor and a power supply. The delivery device can periodically charge the capacitor via the power supply and periodically discharge the capacitor by operating the motor.

In some embodiments that include a capacitor, the delivery device can periodically discharge the capacitor by powering the at least heating element.

In some embodiments that include a capacitor, the delivery device can sequentially discharge the capacitor by operating the motor and powering the at least one heating element and recharge the capacitor between operating the motor and powering the at least one heating element.

In some embodiments, the processor can be coupled to the motor. The processor can generate and provide pulses to the motor for powering the motor. The reusable part can include a revolution counter. The device can detect an occlusion if the flow detector determines a condition of no flow in the delivery tube and there is a mismatch between pulses generated by the processor and a predicted number of motor revolutions.

In some embodiments, the delivery device, upon sequential operations of motor and flow detector, can detect air bubbles within the delivery tube and/or an occlusion in the delivery tube.

In some embodiments, the at least one heating element can be proximate to the delivery tube at a first location. The at least one heating element can directly heat the delivery tube to cause heating of the therapeutic fluid in the delivery tube. An upstream temperature sensor can be upstream of the first location. A downstream temperature sensor can be downstream of the first location.

In some embodiments, the delivery device can determine flow rate of therapeutic fluid within the delivery tube based, at least in part, on temperature measurements measured by the at least one upstream temperature sensor and the at least one other downstream temperature sensor.

the flow detector can further comprise an alignment rack. The alignment rack can hold the at least one heating element, the at least one upstream temperature sensor, and the at least one downstream temperature sensor. The alignment rack can move the heating element, the at least one upstream temperature sensor, and the at least one downstream temperature sensor alternatively to proximate to the delivery tube, and in contact with the delivery tube.

In some embodiments, the delivery tube can be resilient, i.e. elastic or flexible. Such a delivery tube can have the particular property of compensating for tolerances, thus ensuring reliable contact of the tube with heating elements and temperature sensors.

In some embodiments, the flow detector, in response to a determination that there is no fluid flow, can identify one or more of several possible problems causing the condition of no fluid flow. The several possible problems can include: a missing pulse of the motor operation, a reservoir of the therapeutic fluid being empty, presence of air bubbles in the delivery tube, occlusion occurring in the delivery tube and the like.

In some embodiments, the delivery device can adjust or control delivery of the therapeutic fluid through the delivery tube based on determined flow such that the therapeutic fluid can be delivered at a substantially pre-determined delivery rate.

According to a further aspect, a reusable part for use in a portable therapeutic fluid delivery device in combination with a disposable part is presented. The reusable part can include a driving mechanism, the driving mechanism including a rotary motor and at least one gear; a flow detector comprising the at least one heating element and at least two temperature sensors, and a processor. The reusable part can pair with the disposable part such that upon pairing of the reusable part with the disposable part, the heating element and the at least two temperature sensor touch a delivery tube of the disposable part. The processor, upon activation of the at least one heating element, can detect a flow condition of the therapeutic fluid inside the delivery tube.

According to a still further aspect, a disposable part for use in a portable therapeutic fluid delivery device in combination with a reusable part is presented. The disposable part can include a reservoir, an exit port, and a delivery tube communicating between reservoir and exit port. The disposable part can pair with the reusable part such that upon pairing of the reusable part with the disposable part a heating element and at least two temperature sensors of the reusable part can touch the delivery tube.

According to a still further aspect, a therapeutic fluid delivery device kit is presented. The kit can include a reusable part and at least two disposable parts. The reusable part and any of the disposable part can form a skin adherable drug dispensing unit.

In some embodiments, the kit can further includes at least two skin adherable cradle units. The drug dispensing unit can disconnect from and reconnected to the cradle unit.

According to a still further aspect, a method for determining a flow condition of therapeutic fluid in a two part portable fluid delivery device is presented. The method can comprise providing a reusable part that can include a rotary motor and a flow detector. The flow detector can include at least one heating element and at least two temperature sensors. A disposable part can be provided. The disposable part can include a reservoir, an outlet port, and a delivery tube that is communicating between reservoir and exit port. The reusable part and the disposable can pair such that the flow detector can touch the delivery tube. The flow detector can operate consecutive to an operation of the motor at a predetermined number of operation cycles. The flow condition can be determined based on a signal provided by the at least two temperature sensors.

In some embodiments, the method can include determining a temperature gradient within the therapeutic fluid and determining the flow condition based on the temperature gradient.

In some embodiments, the method can comprise heating the therapeutic fluid in the delivery tube at a first location. A temperature of the therapeutic fluid can be measured at least at an upstream location and a downstream location from the first location. A temperature gradient can be determined within the therapeutic fluid. The flow condition can be determined based on the determined temperature gradient.

In some embodiments, the method can, in response to a determination that there is no fluid flow, identify one or more of several possible problems causing condition of no fluid flow. The several possible problems can include a missing pulse of the motor operation, a reservoir of the therapeutic fluid being empty, presence of air bubbles in the delivery tube, occlusion occurring in the delivery tube and combinations thereof.

According to a still further aspect, a method for delivering a therapeutic fluid into a patient's body via a portable fluid delivery device can comprise determining a flow.

In some embodiments, the method can include delivering power to the at least one heating element; suspending power delivery to the at least one heating element; and delivering power to the motor of the pump to begin motor operation subsequent to the suspension of power delivery to the heating element. The power delivered to the motor can cause the heated therapeutic fluid to flow in the delivery tube.

In some embodiments, the method can include adjusting the delivery of the therapeutic fluid through the delivery tube such that the therapeutic fluid can be delivered at a substantially pre-determined delivery rate.

A method for determining a flow condition or a method for delivering a therapeutic fluid to a patient may be carried out using a delivery device. Vice versa, a delivery device may carry out any of the methods. Therefore, any feature or embodiment that is disclosed and discussed in a device context may be used for detailing a corresponding method claim and vice versa.

The processor of a device can be coupled to the motor and can control its operation. It can be advantageously to be further coupled to the flow detector and can control operation of the flow detector and processes and can evaluate the signals provided by the flow detector, in particular by the temperature sensors. The processor may further be used for additional purposes such as controlling a user interface and telemetry interfaces for communicating with a remote control unit and/or further external devices, such as a PC. The term "processor" or, interchangeably, "controller" can be used in the sense of electronic circuitry that can be typically based on one or microprocessors or microcontrollers and/or ASICS. The processor may further include or be coupled to additional circuitry and/or functional units such as power supply circuitry, safety circuitry, timers, clock circuitry analogue-to-digital (AD) conversion circuitry, and the like. The processor may be realized by a single or a multiple of distinct components.

Fluid may be administered in a programmed pulsed delivery pattern (hereinafter "delivery pulses" or "delivery pulse mode"—predetermined quantum (delivery pulse) at every predetermined period, for example about 0.05 insulin units (U) every 30 minutes). Thus, fluid may be administered in a pulsatile wave form (delivery pulses), thus realizing a quasi-continuous delivery. The delivery pulses can be changed at the patient's discretion or according to feedback from one of the detectors. The flow detector can determine a flow condition of the therapeutic fluid in the delivery tube. The flow condition may include a determination whether or not there is fluid flow in the delivery tube and/or determining a flow as amount per time. The flow condition may further include derived information such as a determination whether or not a flow is above or below a given flow threshold value.

For embodiments that are based on a pulsed fluid delivery, the flow detector may measure the volume of fluid or detecting a flow condition in, for example, each delivered pulse. The data may be used by the processor to adjust the volume in each quantum (delivered pulse) and/or the intervals between delivered pulses based on the received measured data. Additionally or alternatively, the data provided by the flow detector may be used for triggering an alarm in case of a defect, malfunction, or hazardous situation, such as air bubbles in the delivery tube, an occlusion or a leakage.

In some embodiments, reservoir can be a cartridge with a displaceable plunger and the motor can be coupled to the plunger via a threaded drive screw/spindle. The plunger can be displaced in a controlled way similar to a syringe mechanism in response to axial rotation of a threaded drive screw, resulting from motor operation. In some embodiments, the drive screw can have a distal end that can be substantially rounded or spherical in shape and can articulate with the plunger and a proximal end that can engage with a rotating gear connected to the motor. In such embodiments, the plunger can have a distal end which can contact the fluid within the reservoir and at least one gasket to prevent leakage of fluid from the reservoir. The plunger may also include a proximal end comprising a socket that articulates with the rounded distal end of the drive screw. The socket may be shaped to interact with the distal end of the drive screw. A drive nut with internal threads may also be provided for engagement or disengagement with the drive screw. For example, in an engaged position, rotation of the drive screw within the drive nut can linearly displace the drive screw and, in turn, the plunger can articulate therewith. In a disengaged position, the drive screw may freely move within the drive nut and can be manually pushed backward for reservoir filling or pulled forward for reservoir priming.

In some embodiments, the device can comprise a two-part skin securable drug dispensing unit, a skin adherable cradle unit, and a remote control unit. The drug dispensing unit can be disconnected and reconnected from and to the cradle unit. A connecting lumen can provide fluid communication to a cannula rigidly connected to the cradle unit. Fluid delivery can be remotely controlled by the remote control unit or, alternatively or additionally, by manual buttons located on the dispensing unit.

The cradle unit may include a flat sheet with an adhesive surface, a passageway for a cannula, and snaps for securing the cannula and dispensing unit. The cannula can include a distal end residing in the body and a proximal end that may include a self-sealed rubber, thus forming a sealing pierceable septum. The cannula can manually, or automatically, be inserted into the body using a penetrating member for skin pricking. After insertion, the cannula can be secured to the cradle unit with snaps located near the cradle passageway (cradle and cannula hereinafter "infusion set"). The drug dispensing unit can be connected and disconnected from the cradle unit. During connection, a connecting lumen within the skin adherable unit can pierce the cannula septum maintaining fluid communication between the reservoir, drug delivery tube, and the body.

Such a configuration including a skin securable dispensing unit and a cradle can be particularly convenient and flexible in use. The costs can be comparatively low due to the partly reusable design. Other configurations however may be used as well. For example, an adhesive pad may be directly provided on the disposable part such that the disposable part and the reusable part, once paired, can be directly attached to the skin. For such embodiments, the disposable part may include the cannula or a cannula may be provided separately. Furthermore, the fluid delivery device may be carried in a pager-like way rather than attached to the skin and a cannula may be coupled to the device via tubing.

A remote control unit may comprise a handheld device for programming fluid flows, generally controlling the device, in particular a patch unit, acquiring data, and providing visual and/or audible and/or vibration notifications. In some embodiments, the remote control unit may include without limitation a wrist-watch, a cellular phone, a personal digital assistance ("PDA"), an iPhone or iPod, a personal computer (PC) or a laptop computer. In some embodiments, the remote control unit may include an integrated blood glucose monitor, such as an optical refractometer-based or electro-chemical blood glucose monitor, as generally known in the art. Such monitors can be used in a combination with test strips that are typically disposable and single-use.

In some embodiments, the delivery device can include a skin securable drug dispensing unit which can include a blood glucose monitoring unit. The blood glucose monitoring unit may be based on an electro-chemical sensing principle as generally known in the art and may accordingly include a corresponding sensing probe.

In some embodiments, the disposable part may contain a power source (e.g., batteries) which may serve as primary power source for the device or the application time of the disposable part, i.e., typically some days. Alternatively or additionally, a power source, typically in form of a rechargeable or non-rechargeable battery, may be included in the disposable part.

In some embodiments, the reservoir may be a cartridge including a plunger and may have a flat profile (e.g., oval, ellipse, or four or eight arches) to provide a thin configuration as compared to a circular profile.

In some embodiments, the reusable part and disposable part may each have an external housing (e.g., shell) and an internal structure (e.g., chassis), where the external housings and internal structures can be coupled when the reusable part and disposable part are connected. The housings of both parts may have an opening that provides contact between disposable part and reusable part internal structures (chassis).

The delivery tube may be made of a resilient material and may be wrapped around the disposable part chassis such that a portion of the loop is facing the reusable part chassis and can contacts the flow detector included in the reusable part. For such an embodiment, connecting or pairing of the reusable part and disposable part can cause the following: 1) the reusable part's and disposable part's external housings and internal structures are coupled together, thus resulting in the drive nut to move from a disengaged position to an engaged position to thus engage the threads of the drive screw with the threads of the drive nut, 2) engagement of the proximal end of the drive screw with the gear located within the reusable part, 3) engagement of the delivery tube of the disposable part with the non-disposable components of the flow detector, i.e., the at least one heating element and the temperature sensors of the reusable part. In embodiments where the disposable part includes a power supply that also supplies the reusable part, electrical contact may be established during pairing as well.

The delivery device may, besides the flow detectors, include either or multiple of the following detectors:

- A motor errors and/or or a motor supervision detector—a detector designed to perform detection of missing motor train pulses. This detector may be include a rotary encoder or revolution counter, e.g. on an optical or magnetic basis.
- An end of reservoir detector—a detector designed to perform detection of remaining volume of therapeutic fluid (drug) in the reservoir.
- Occlusion detectors (e.g., two detectors)—Such detectors are designed to perform detection occlusion in drug delivery path. One detector may be based on counting missing pulses and another occlusion detector may be based on monitoring flow in the delivery tube (e.g., using, for example, a flow detector).
- An air bubbles detector—Such a detector is configured to perform detection of air bubbles in the drug delivery path.
- A leakage detector—detection leakage in drug delivery path.

The term "detector" can be used in the sense of a functional unit that may include hardware and/or firmware or software based components. Software or firmware based components may be, fully or partly, be implemented by the processor of the delivery device and/or spate dedicated circuitry. Furthermore, detectors may, fully, or partly, make use of the same physical sensors.

As described herein, in some implementations detection of occlusion, air bubbles, and leakage may all be based on signals that are provided by the flow detector.

Two temperature sensors can be located symmetrically, at pre-defined substantially equal distance from the heating element (e.g., one upstream of the heating element, the other downstream of the heating element). After connection of the disposable—reusable parts, the heating element and temperature sensors (e.g., a resistor that change resistance according to temperature changes, for example a thermistor) can come in contact with the delivery tube in a way that can ensure reliable thermal coupling. A thermistor or thermal sensor can be a type of resistor whose resistance varies significantly with temperature, more so than in standard resistors. Most PTC thermistors can be the "switching" type, which means that their resistance rises suddenly at a certain critical temperature. Another type of PTC thermistor can be the polymer PTC which can have a highly nonlinear resistance/temperature response and can be used for switching, not for proportional temperature measurement. Yet another type of thermistor can be a silistor, a thermally sensitive silicon resistor. Silistors operate on the same principles as other thermistors, but employ silicon as the semiconductive component material.

Activation of the heating element can cause temperature elevation of fluid within a portion of delivery tube that comes in contact with the heating element and consequently formation of an upstream (direction of flow) and a downstream (opposite direction of flow) temperature gradients. Since thermal coupling of the fluid and the heating element and temperature sensors can be achieved via the delivery tube, a temperature gradient can also be formed in the delivery tube. The distribution of temperature gradient can be related to the drug flow within the delivery tube and thus to the flow rate and flow volume (dose). In the absence of fluid flow, the temperature gradient can be substantially symmetrical relative to the heating element and the electrical signal from both temperature sensors (e.g., temperature-sensitive resistors) can be substantially equal (manifested as equal electrical resistance when temperature-sensitive resistors are used to measure temperature). In the presence of (fluid) flow, the temperature distribution around the heating element can become asymmetric (temperature gradient can be skewed towards the direction of flow) leading to different signals from temperature sensors. The difference in signal can be correlated, e.g. in a proportional way, to the speed of liquid movement (flow). The expected flow rate (in the absence of any obstruction or leakage) can be determined based, at least in part, on the known dimensions and physical properties of the delivery tube, thermal energy generated by the heating element, the rate or level of pumping actuation caused by the pumping mechanism, and the like.

The volume of flow (e.g., drug dose) can thus be derived from, for example, computation of the area under the curve of time versus temperature differences and/or by evaluating the slope of this curve. Operation of the heating element can be adjusted in an energy saving mode, for example short heating (milliseconds) period that precedes motor operation by a predetermined time interval and monitoring temperature gradient for a short period after motor operation. The delivered dose can be computed, for example, by the processor of the delivery device. The result can be used in some embodiments to automatically adjust motor operation in a positive or negative feedback (more or less motor operation time in one or more consecutive motor operations).

Occlusion and air bubbles can be detected by the flow detector based on a determination that there is no flow within the delivery tube. If no flow is detected notwithstanding the operation of the motor, the patient may be, for example, notified to take appropriate remedial action (such as removing the skin adherable dispensing unit from the cradle unit). If air bubbles are visually detected, air purging may be performed and the dispensing unit reconnected. Detection of no flow when the reservoir is full or partially full and air bubbles are missing can mean that there is an occlusion within the delivery path and the infusion set (cradle and cannula) should be replaced.

In summary, the flow detector can be used for quantitative measurement and/or for qualitative supervision and monitoring purposes. In the first case, the quantitative results may be monitored, and, e.g. stored or logged in a device memory and/or may be used for closed loop control of the delivery device. In the latter case, the evaluation of the flow detector signal results in a binary signal that can be indicative for the presence or absence of a defect, malfunction or hazardous situation and can be favorably used for triggering corresponding alarms.

The flow detector data may be evaluated alone and/or may merged and evaluated in combination with signals that can be provided by further sensors or detectors, such as a rotary encoder or revolution counter.

Referring initially to FIG. 1a, FIG. 1a is a schematic diagram of an embodiment that can include a device 10 for delivering therapeutic fluid into the body and for monitoring analyte levels within the body and a remote control unit 40 for controlling the device 10 and for data acquisition. The remote control unit 40 may communicate (via a wire-based communication link and/or a wireless communication link) with other external devices such as blood glucose monitors (BGM), continuous glucose monitors (CGM), personal computers (PC), and the like. In some embodiments, the device 10 is realized by a skin securable drug dispensing unit. The drug dispensing unit 10 may include one part (as shown, for example, in FIG. 1*b*) or two parts (as shown, for example, in FIG. 1*c*). In the latter case, the drug dispensing unit 10 can include a reusable part 100 and a disposable part 200. The drug dispensing unit can include a fluid dispenser that can be operated by the remote control unit 40 which may, or may not include an analyte monitor, such as a blood glucose monitor. The drug dispensing unit may or may not include a blood glucose measuring unit for continuous or substantially continuous measuring the patient's blood glucose level. The drug dispensing unit 10 may be programmed with the remote control unit 40 or by using buttons placed on the drug dispensing unit (such as a button 15 shown, for example, in FIG. 2).

Therapeutic fluid (e.g., insulin) can be administered at the following delivery patterns:

1) A bolus dose, which is a dose delivered to counterbalance meal's carbohydrates consumption and/or high blood sugar. The pattern of a bolus dose, in particular the distribution of the delivery over time, can be programmed according to, for example, glycemic index and fat content of a meal (e.g., after a pizza meal a dual wave bolus pattern is recommended to immediately "cover" the fast absorption of carbohydrates and slow absorption of fat).
2) A basal dose or basal rate, which is a substantially continuous administration of insulin A basal rate may be provided as a series of pulses of administered insulin to counterbalance internal glucose production and counter regulatory hormones (glucagon, adrenalin, etc.). A basal rate can be changed during the day according to a patient's activity and hormonal activity. A corresponding time profile, typically a circadian profile, may be stored in the drug dispensing unit 10 and/or the remote control unit 40.
3) A combination of bolus and basal doses. In order to mimic the normal function of the human pancreas, the drug dispensing unit 10 may be configured to administer insulin basal doses at short delivery intervals. For example, if the delivery rate is 1.0 units/hour (1 U/h) the patch unit can be programmed to administer 0.05 U every 3 minutes (20 deliveries/hour), thus 20 consecutive administrations of 0.05 U at intervals of 3 minutes equals 1.0 U/h.

Figure 2B:
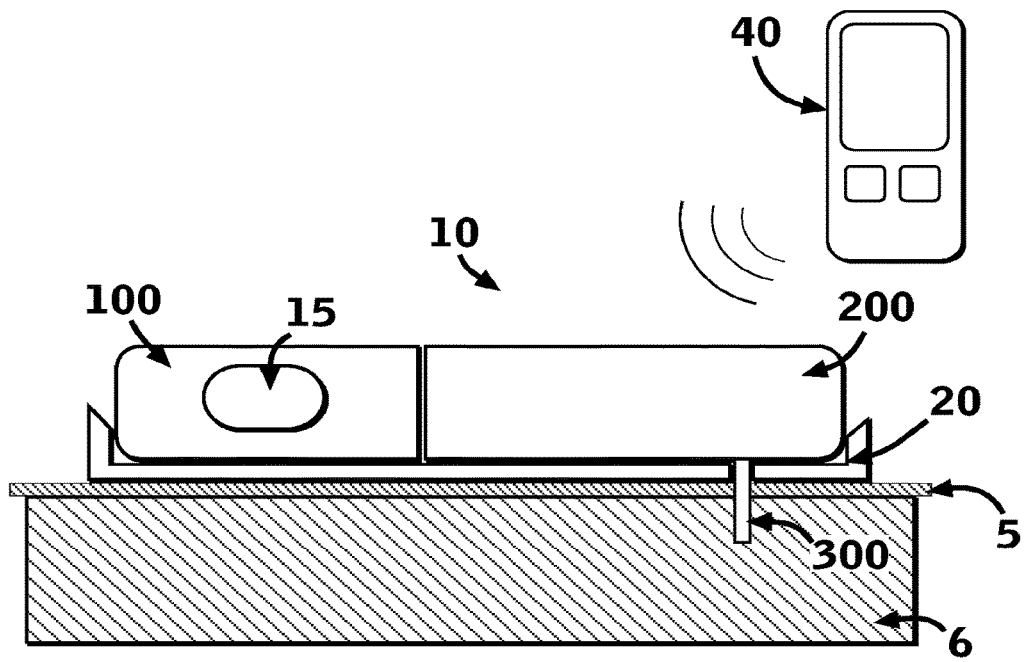

FIGS. 2*a*-*b* show the skin securable drug dispensing unit 10 connected to a skin adherable cradle 20 that can be adhered to skin with an adhesive 5. The drug dispensing unit 10 may be disconnected from and reconnected to a cradle unit 20 and may comprise one part (as shown, for example, in FIG. 2*a*) or two parts (as shown, for example, in FIG. 2*b*). In the latter case, the drug dispensing unit 10 can include a reusable part 100 and a disposable part 200 as discussed above.

A tip 300 can be provided to deliver fluid (e.g., insulin) into the body and/or to monitor analytes (e.g., glucose) within the body. The tip 300 may include a cannula for fluid delivery and optionally a probe for analyte sensing. The tip 300 can be inserted through a cradle opening into the subcutaneous tissue 6. Commands for dispensing fluid can be communicated via the remote control unit 40 or by one or more buttons 15 located on the patch unit 10. In some embodiments, the buttons may include a bolus button(s) triggering the delivery of a bolus volume of fluid (e.g., insulin) into the body.

Figure 3:
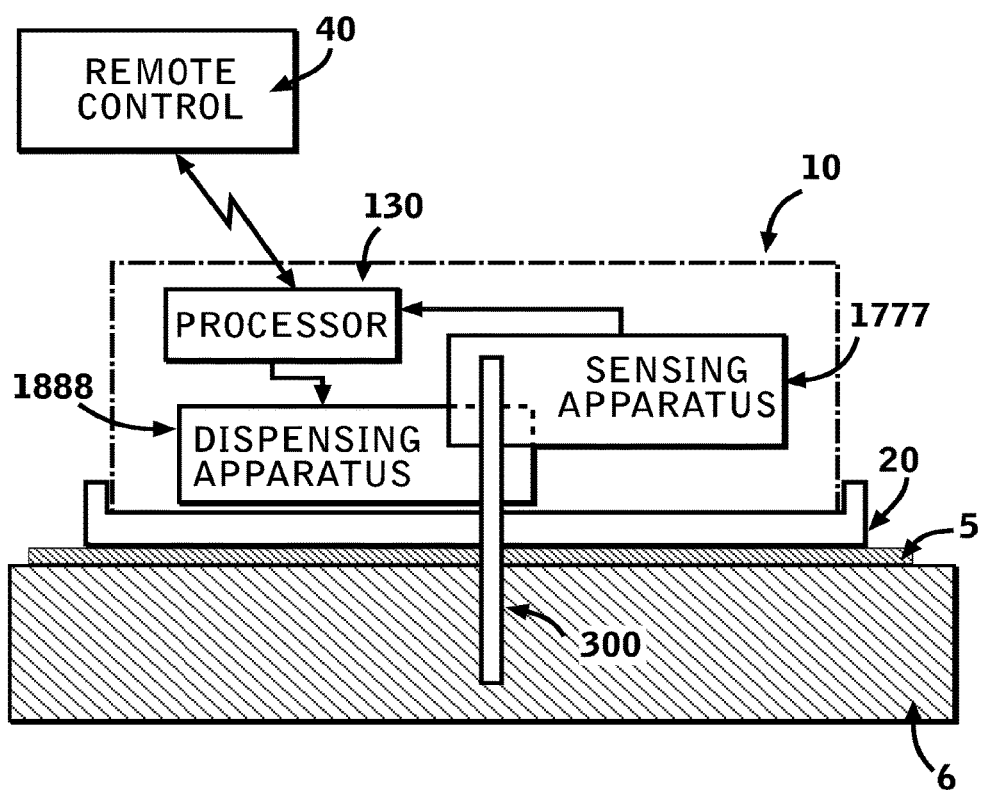
FIG. 3 illustrates an example therapeutic and monitoring system that includes a remotely controlled patch according to an embodiment of the present disclosure.

FIG. 3 is a schematic diagram of an example system. The drug dispensing unit 10 can be secured to a skin adherable cradle 20 connected to skin with adhesive 5. The patch unit 10 can include a dispensing apparatus 1888 for delivery of fluid into the body and a sensing apparatus 1777 for monitoring analytes within the body. The dispensing apparatus 1888 in particular can include a drive mechanism with gear and a reservoir. The sensing apparatus 1777 may include a blood glucose measuring unit.

Tip 300 can be inserted through passageway in cradle 20 into the subcutaneous tissue 6. Processor 130 can be provided for one or more of the following tasks: 1) to receive analyte readings from the sensing apparatus 1777, 2) to control operation of the sensing apparatus 1888, 3) to communicate with remote control unit 40, and 4) to process received internal or external data. In some embodiments, the fluid can be insulin and the analyte can be glucose.

The therapeutic and monitoring system can be operated at either or more of the following modes:

1) Closed loop system—the processor 130 can receive glucose readings from sensing apparatus 1777 and can automatically control insulin delivery from the dispensing apparatus 1888 based, at least in part, on the received glucose readings.
2) Open loop system—the processor 130 can receive glucose readings from the dispensing apparatus 1777 and can control insulin dispensing between meals. The processor 130 can also receive dispensing commands from the remote control 40 (provided, for example, by the user) before meals.
3) No linkage between dispensing and sensing apparatuses—glucose readings can be presented to the user (e.g., via a screen on the remote control, a screen on the pump). Insulin administration control commands can be provided (e.g., programmed) via the remote control unit 40 or buttons on the patch unit (not shown in FIG. 3).

Figure 4:
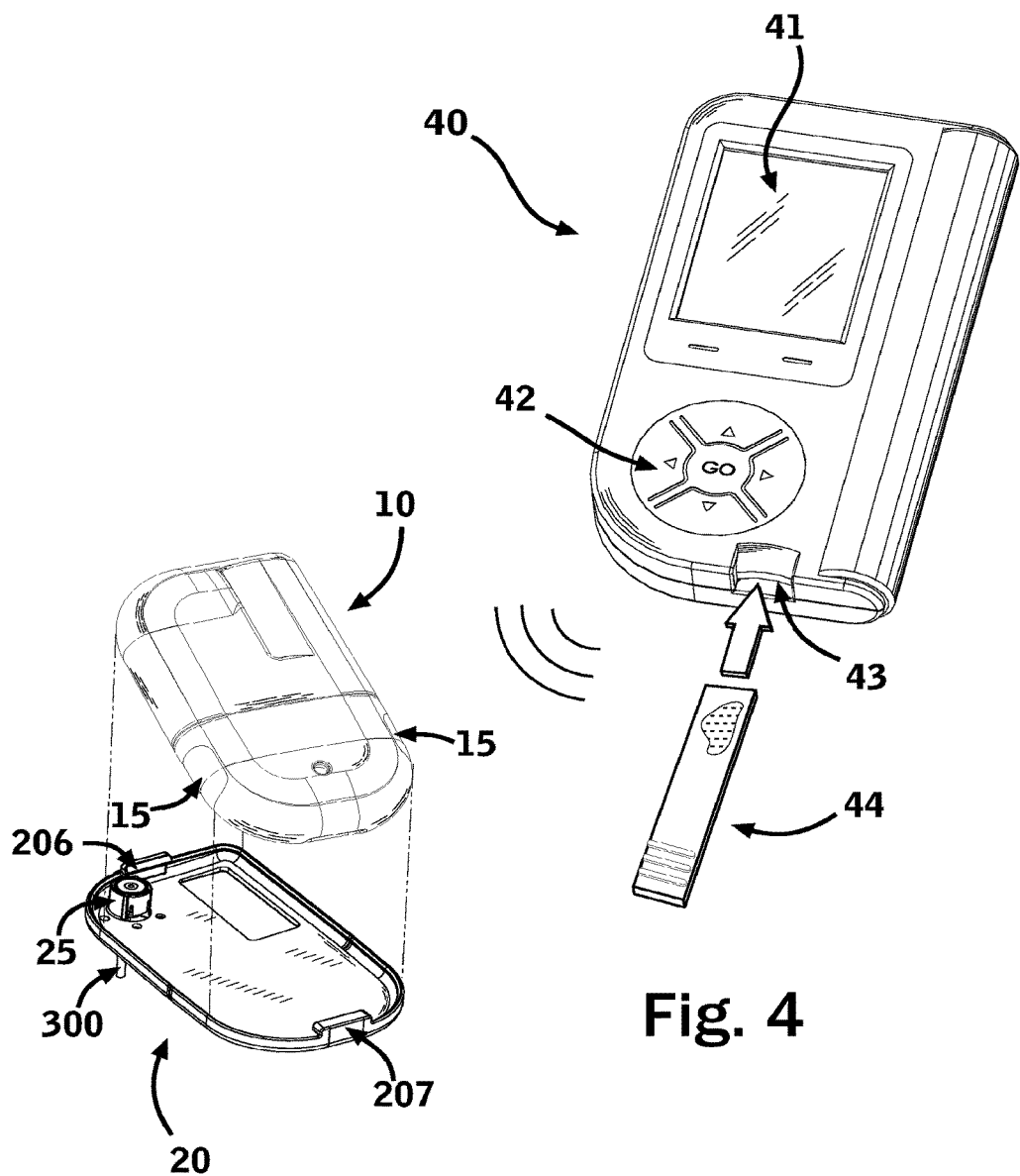
FIG. 4 illustrates a perspective view of an example therapeutic and monitoring system with a remote control that includes an integrated blood glucose monitor according to an embodiment of the present disclosure.

FIG. 4 is a diagram showing a spatial view of an example therapeutic and monitoring system. The remote control 40 may include an integrated blood glucose monitor. The remote control 40 can comprise a screen 41, a keypad 42, and a slot 43 to receive a blood test strip 44. The remote control 40 can be used for programming the drug dispensing unit 10, acquiring data from the patient, and communicating with other electronic devices (e.g., computers) to carry out, for example, data downloading and uploading. The cradle unit 20 can comprise a flat sheet having a surface that can be adherable to the skin of a patient. The cradle unit 20 may also comprise a passageway for inserting a tip 300 into the body and protrusions 206 and 207 (e.g., snaps) for securing the patch unit 10 to the cradle 20. A protrusion 25 (also referred to as a "well") surrounding the passageway provides rigid connection of the tip 300 to the cradle 20. Insertion of the tip 300 may be performed manually or via a dedicated inserter.

In some embodiments, a device may include a drug dispensing unit or patch unit (e.g. an insulin dispensing patch unit) and an analyte sensor (e.g. a continuous glucose monitor as shown in FIG. 4 and described above, and may also be disconnected from and reconnected to the body at a patient's discretion.

In some embodiments, fluid may be dispensed according to blood glucose levels in the body and thus the device may function as an automatic or closed-loop system. In some embodiments, the device may function as a semi-automatic or open-loop system, where additional inputs from the user (e.g., meal times, changes in basal insulin delivery rates, or boluses before meals) can be used in a procedure to determine the amount of fluid to be delivered by the device in conjunction with inputs from the analyte sensor.

Figure 5:
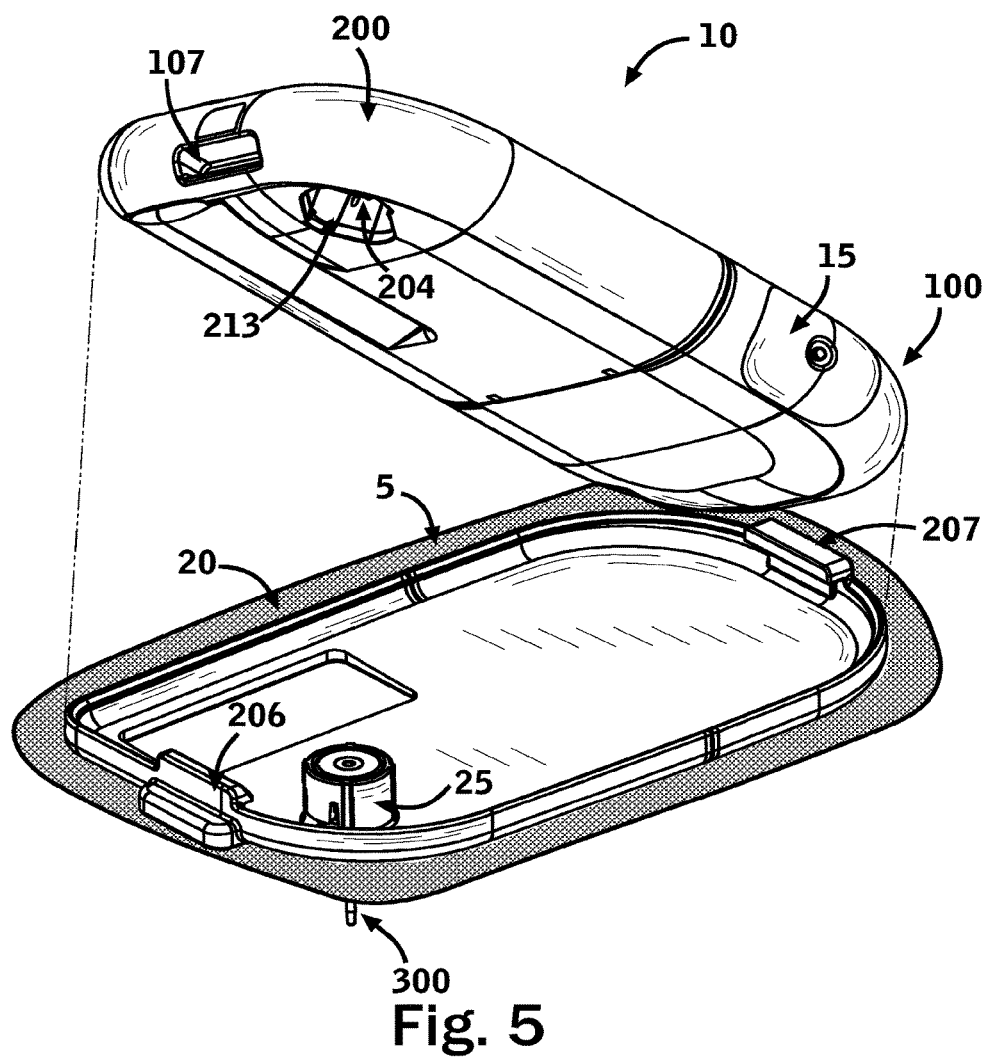
FIG. 5 illustrates a perspective view of an example two part patch unit and cradle according to an embodiment of the present disclosure.

FIG. 5 is a schematic diagram showing a perspective view of the drug dispensing unit 10 and the cradle unit 20. The drug dispensing unit 10 can include a reusable part 100 and a disposable part 200 and two recesses 107 at both sides of the drug dispensing unit 10 (only the front recess is shown in FIG. 5). Buttons 15 on the reusable part 100 can provide insulin delivery programming and administration commands without the remote control unit. The disposable part 200 can include a reservoir (not shown), an exit port 213, and a connecting lumen 204. The cradle unit 20 can comprise a flat sheet connected to a skin adherable adhesive tape 5 and snaps 206 and 207. A well 25 can be a protrusion surrounding a passageway within cradle flat sheet. A tip 300 can be inserted through well 25 and cradle passageway and can rigidly connect to the well 25 after insertion. Insertion can be done manually or automatically with an inserter device. In some embodiments, during connection of the drug dispensing unit 10 and the cradle unit 20, the exit port 213 can align with the well 25 and the connecting lumen 204 can pierce a rubber septum located at the proximal part of tip 300 providing fluid communication between the reservoir and the tip 300. Snaps 206 and 207 can secure the patch unit 10 within cradle unit 20 by alignment with the front recess 107 and the rear recess (not shown).

FIGS. 6a-d are cross sectional views of a cradle unit 20 and an adhesive 5 after insertion of a tip 300 through a well 25 into a body 6 (i.e. subcutaneous tissue). The cradle unit 20 can comprise snaps 206 and 207 for securing a patch such as the drug dispensing unit 10 (not shown).

FIG. 6a shows the normal position of tip 300 within the body 6. In this configuration, the tip (comprising a cannula) 300 can be substantially perpendicularly positioned within the subcutaneous tissue, providing smooth fluid delivery.

FIGS. 6b-d show three cannula malfunctions that hamper fluid delivery. In diabetes therapy, the patient insulin should be continually administered and insulin delivery shutdown can cause elevation of blood glucose, keto-acidosis, and, potentially, death. FIG. 6b shows an occlusion of cannula 300 due to obstruction of foreign material (i.e. dislodged fat tissue, insulin crystallization, etc). FIG. 6c shows kinking of cannula 300 that can happened during insertion, for example, when hitting scarred tissue. FIG. 6d shows a complete folding of the cannula 300 underneath cradle 20. This situation can occur during cannula 300 insertion or if cannula 300 is spontaneously dislodged from the body 6 and the patient repositions the cradle 20. All of those hazardous conditions can be detected by providing a delivery device with a flow detector in accordance with the present disclosure.

Figure 7A:
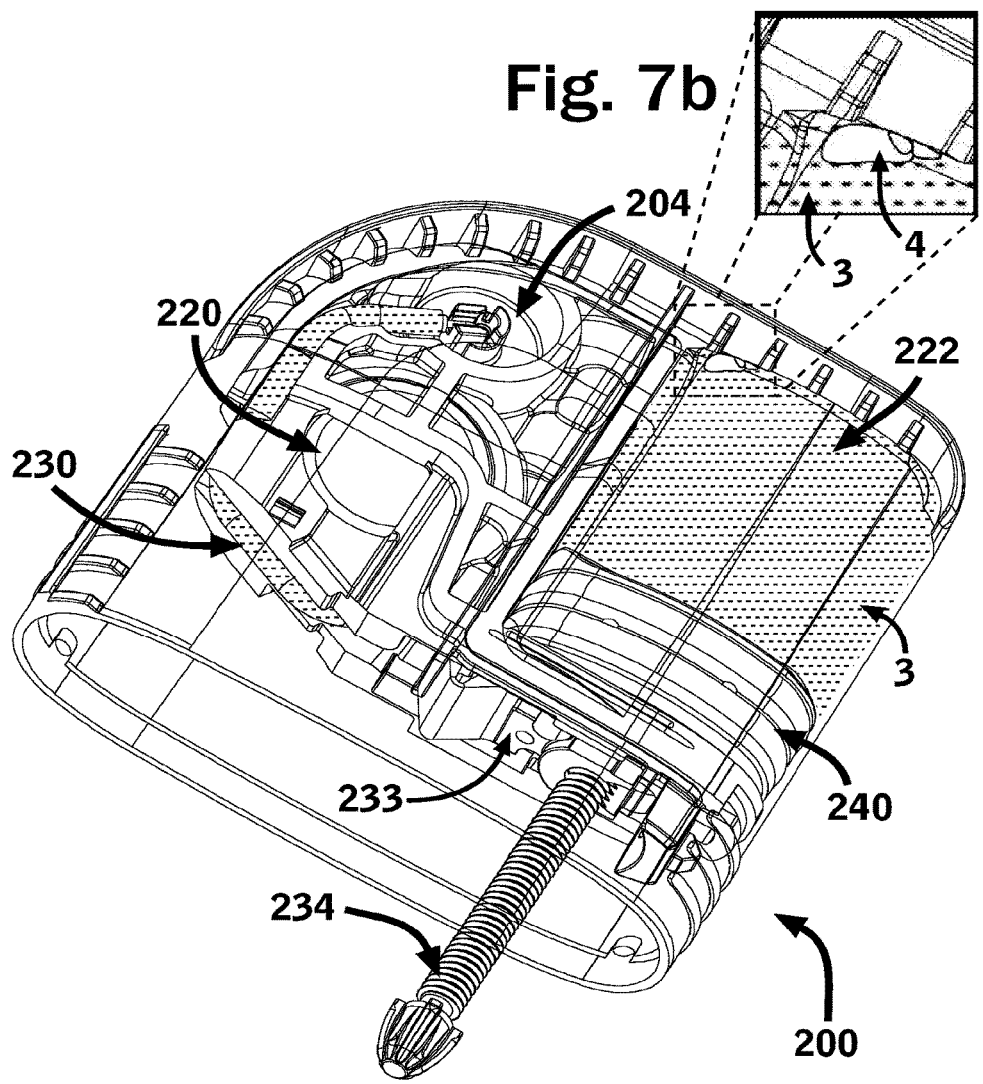

FIGS. 7a-b show a diagram of the disposable part 200 that comprises a reservoir 222 filled with therapeutic fluid 3 (e.g., insulin). The disposable part 200 can include a plunger/piston 240 slideable within the reservoir 222 and can force fluid 3 to be expelled from the reservoir 222 into the delivery tube 230 and from the delivery tube 230 to an exit port 213. A drive screw 234 can serve as plunger/piston rod. Clockwise or counterclockwise rotation of drive screw 234 can be converted by nut 233 to forward or backward linear motion. Rotation of drive screw 234 can be provided by engagement of a drive screw tip with reusable part gear (not shown) after pairing the reusable and the disposable parts. In some embodiments, the disposable part 200 can include a power source 220 (e.g., one or more batteries). Upon paring, the power source within the disposable part 200 can supply energy to the electronics components and the motor located in the reusable part. In other embodiments, the reusable part 100 can include the power source 220.

During reservoir filling and/or during operation air bubbles 4 can be formed in the fluid 3 (e.g., oversaturation during refrigeration storage and bubble formation at room or body temperature). FIG. 7b also shows a magnified view of reservoir upper left corner. An air bubble 4 is located in the reservoir corner and is surrounded with insulin. Further movement of plunger/piston can force air bubble 4 into the delivery tube 230, potentially resulting in no fluid delivery to the body (air is expelled instead of insulin). This situation may also be detected by the flow detector.

Figure 8:
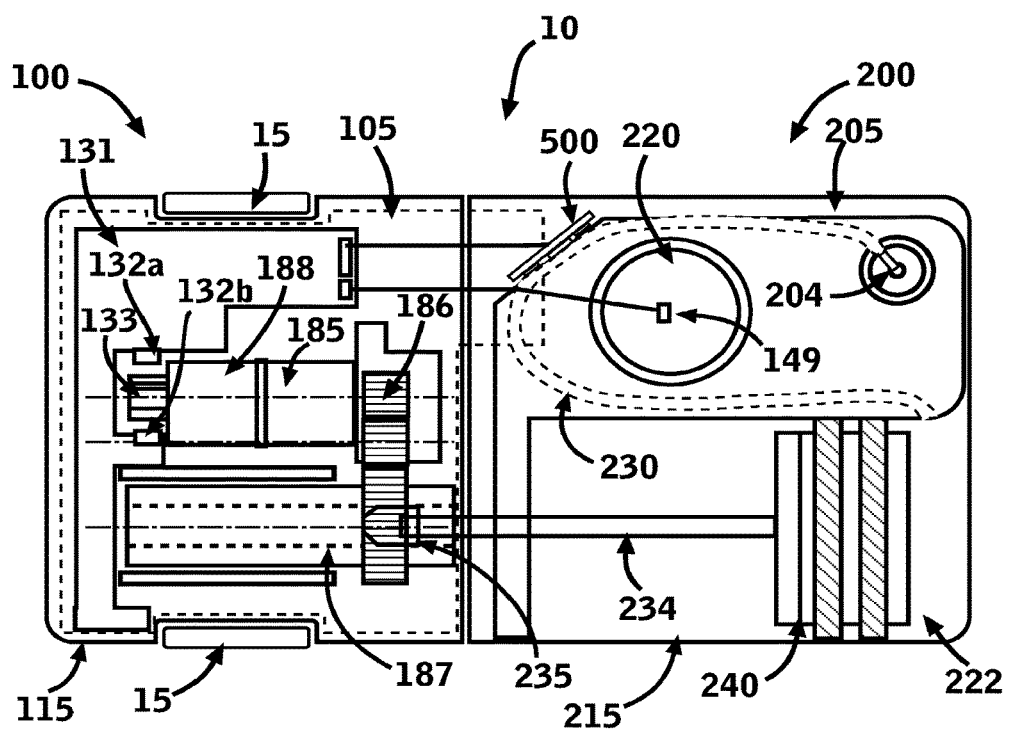
FIG. 8 illustrates a schematic diagram of an example two part patch unit that includes a reusable part and a disposable part according to an embodiment of the present disclosure.

FIG. 8 shows schematically the two-part drug dispensing unit 10, comprising a reusable part 100 and a disposable part 200. The drug dispensing unit 10 can include a pump for dispensing fluid from a reservoir into a patient body. The pump can comprise a driving mechanism that can include the motor and gear, but may alternatively also include a shape memory alloy actuator, a piezoelectric actuator, and the like and a pumping mechanism (e.g., a slideable piston/plunger 240). The pumping mechanism may reside within the disposable part or within both the disposable and the reusable parts. The reusable part 100 and the disposable part 200 can include housings (e.g., shell, pocket) 115 and 215 respectively and can further include chassis 105 and 205, respectively. After pairing is performed, both chassis 105 and 205 can be interlocked and both housings 115 and 215 can be interconnected to thus provide sealing. In some embodiments, at least one of the housing 115 and the chassis 105 of the reusable part 100 can be connected to at least one of the housing 215 and the chassis 205 of the disposable part 200, upon pairing. The reusable part can include a Printed Circuit Board (PCB) 131 (which can include, for example, a processor-based device and other electronic components), a motor 188, and one or more gears 185, 186 and 187. Gear 185 can be, in some implementations, a planetary reduction gear that rotates spur gear 186. Spur gear 186 can rotate gear 187 (hereinafter "rotating sleeve"). The rotating sleeve 187 can have a tubular shape with inward longitudinal protrusions (e.g., star shape). Upon engagement of the rotating sleeve 187 with the drive screw (plunger/piston rod) 234, rotation of the sleeve 187 can cause rotation of drive screw 234. In some embodiments, electrical connectors 149 can provide power to the PCB electronics 131.

In some embodiments, the motor 188 can be a stepper motor. Stepper motors can be widely used in applications requiring accurate position control and compatibility with digital control systems. Electrical pulses of prescribed pulse width and amplitude can advance the motor by a predetermined distance for each pulse. One standard stepper motor type can require 20 pulses (20 consecutive pulses or a "pulse train" of 20 pulses) for one complete revolution, thus providing 18° of revolution per pulse. When a pulse train is supplied to the stepper motor, it can rotate substantially continuously at a rate determined by the pulse repetition frequency. One advantage of a stepper motor can be that its position can be determined by counting the pulses supplied to it, assuming that no slippage occurs.

In some embodiments, motor energy can be supplied by a capacitor that can be recharged between the generations of pulses; energy from one or multiple batteries can be delivered to the capacitor and in response to commands/control signals from the processor (e.g., via a pulse generator) can discharge the stored energy. A defined pulse train (i.e. 20 pulses) can operate (rotates) the motor at defined rotational angle (e.g., 360°) and consequently the motor can rotate the gear (defined reduction ratio, e.g., 1:128). Rotation of the gear can be converted to linear motion of the piston/plunger causing expelling of a defined fluid quantum (e.g., 0.05 insulin units (U)) from the reservoir into the body. Each quantum of delivered fluid can be defined as a delivery pulse. Consecutive generation of pulse trains can operate the motor for a longer duration (higher rotational angle) resulting in a longer linear motion of plunger and larger delivery pulses.

To illustrate, consider the following example:
Pulse trains—3 (3 consecutive 20 pulses)
Motor rotation—3 (each pulse train operates motor at 1 full revolution)
Delivery pulse—0.15 insulin units (U), (each motor rotation expels 0.05 U from reservoir)

Accordingly, in the above example, if a desired basal delivery rate is 0.1 U/h, the administration cycle is 2 delivery pulses of 0.05 U every 30 minutes.

The reusable part housing 115 can include one or more buttons 15 for administration and programming of fluid delivery. The reusable part 100 may contain the following sensors: 1) revolutions counter (e.g., encoder) comprising a rotating pinion 133, a light emitting source (e.g., a LED) 132a and a light detector 132b, 2) a sensor for detection/measurement of flow (flow detector), occlusion (occlusion detector), and air bubbles (air bubbles detector), which may implemented as a single detector (also referred to as "flow detector "500", and 3) end-of-reservoir sensor (e.g., located on the gear 187, not shown). In some embodiments, the flow detector 500 can be used for detecting/measuring the flow rate of the fluid within the delivery tube 230. In other embodiments, the flow detector 500 can be used only for determining a condition of no flow or substantially no flow (e.g., as a result from occlusion, air bubbles, motor malfunction, and the like)

The disposable part 200 can include a power source 220 (e.g., battery), a reservoir 222, a slideable plunger/piston 240, and a plunger/piston drive screw (plunger/piston rod) 234. The drive screw 234 distal tip can comprise a drive screw rotator 235. A delivery tube 230 can maintain fluid communication between the reservoir 222 and the exit port 213. As noted, in some embodiments, when the reusable part 100 and the disposable part 200 are paired, the following can happen: 1) the housings 115 and 215 can connecte to provide a sealing, 2) the RP and DP chassis 105 and 205 can interlocke, 3) the drive screw rotator 235 can engage with gear 187, 4) battery connectors 149 can connecte to the battery 220 to provide energy to, for example, PCB electronics 131 and motor operation 188, and 5) the flow detector 500 can contact the delivery tube 230 to enable flow monitoring of fluid expelling from the reservoir 222 towards the exit port 213.

Figure 9:
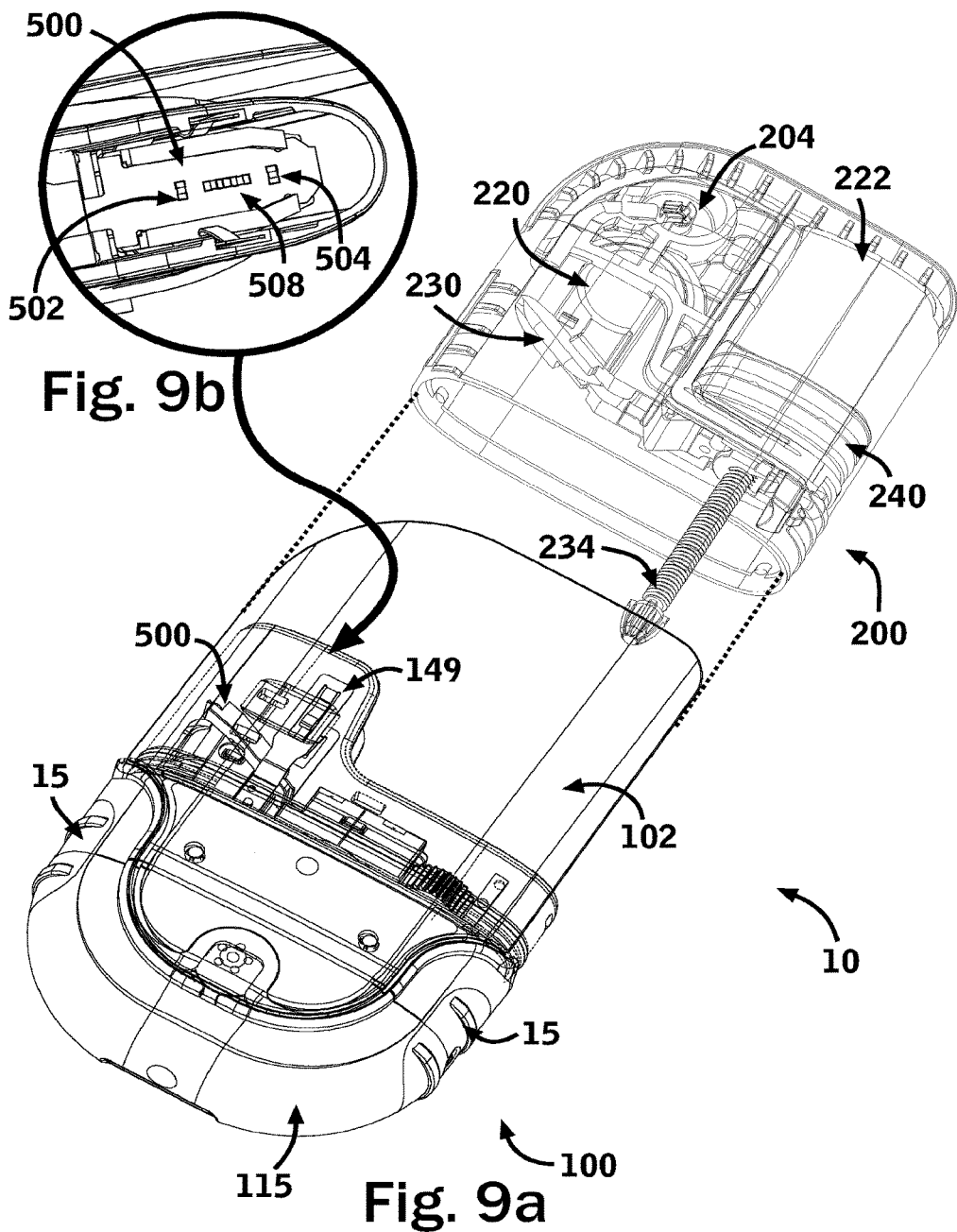
FIGS. 9a-b illustrate a perspective view of an example embodiment of an unpaired two-part patch unit and a magnified view of a flow detector within the reusable part according to the present disclosure.

FIG. 9a shows a perspective view of the unpaired (unmated) two-part drug dispensing unit 10. In some embodiments, the reusable part 100 can include optional operating buttons 15, battery connectors 149, a protective shield 102, and a flow detector 500. The disposable part 200 may include a reservoir 222, a plunger/piston 240, a delivery tube 230, an exit port 213 and a battery 220. FIG. 9b shows a magnified view of the flow detector 500. The flow detector 500 can be located, in some implementations, within the reusable part housing 115 and can include at least one heating element (heater) 508 and one or more, e.g., two, temperature sensors 502 and 504. In some embodiments, after the reusable and the disposable parts are paired the following can happen: 1) the protective shield 102 can cover the reservoir 222 providing impact and pressure protection, and 2) the flow detector 500, including the heating element 508 and the temperature sensors 502, 504, can contact the delivery tube 230.

Figure 10:
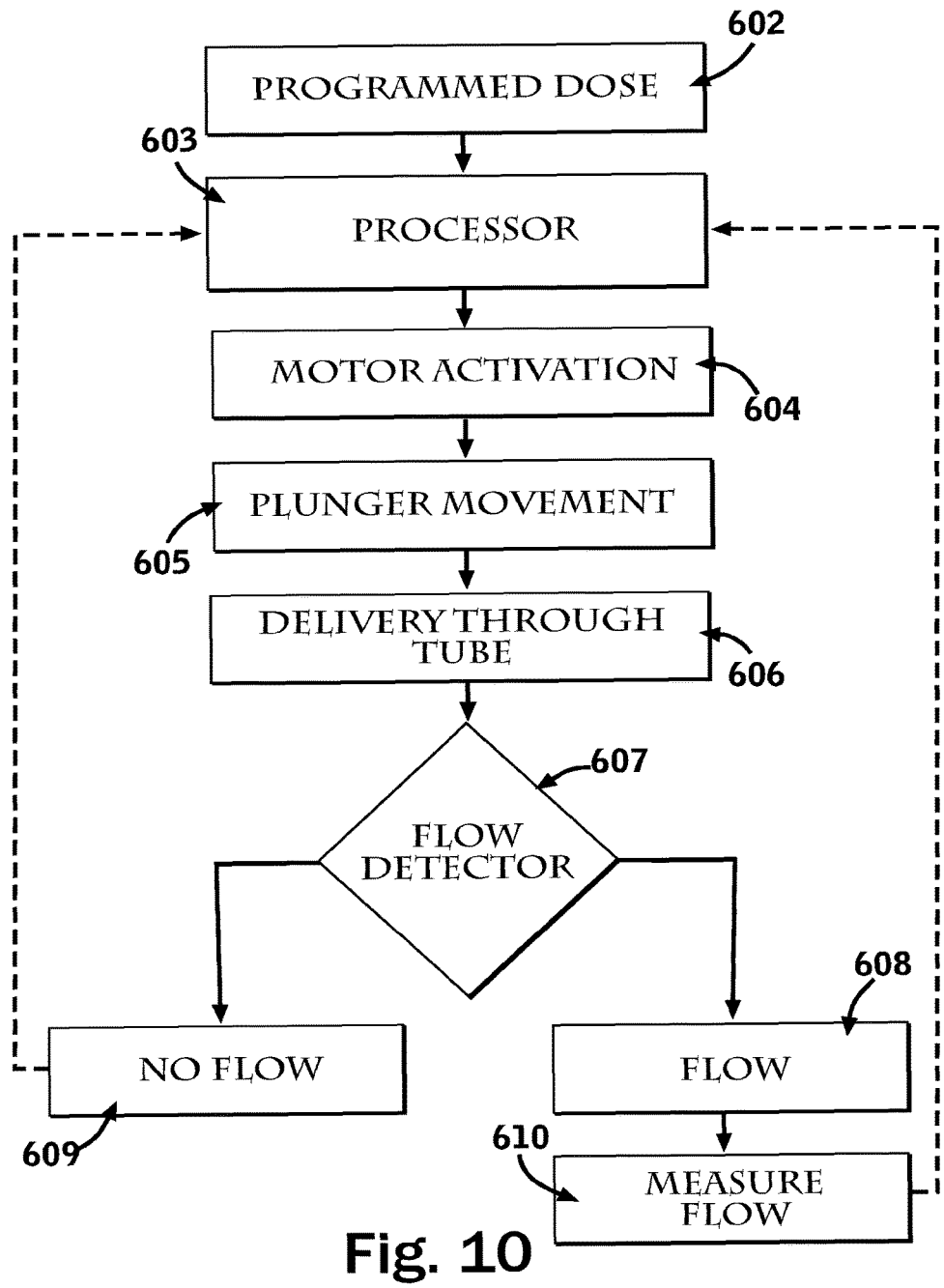
FIG. 10 illustrates a flow diagram of an example feedback control procedure for operation of a dispensing patch unit according to an embodiment of the present disclosure.

FIG. 10 is a flow diagram of an example feedback control procedure to operate the dispensing patch unit (e.g., dispensing apparatus of patch unit). An insulin dose can be programmed 602 with, for example, the remote control or buttons on patch unit (programming a dose may include programming of an amount of insulin, e.g., 5 U, a delivery pattern, e.g., dual wave, square wave, etc., and/or duration to be administered). In some embodiments, a pre-determined insulin dose may be pre-programmed into the patch unit. The programmed dose can be stored in a controller or processor, which can control 604 motor operations according to the stored programmed dose. In some embodiments, the required dose can be delivered in sequential pulses of predefined volume (quantum, e.g., 0.05 U) at predefined intervals (e.g., 30 minutes). For example, a required basal delivery rate of 0.1 U/h can be delivered at delivery pulses of 0.05 U/pulse and an interval of 30 minutes (i.e., 2 per hour). Operation of motor causes plunger movement 605 within the reservoir and consequently insulin can be delivered 606 through a delivery tube. Every motor operation can cause a substantially defined delivery pulse (volume of fluid) to be expelled from the reservoir.

Flow detection 607 can then be performed by a flow detector (e.g., such as the flow detector 500 depicted, for example, in FIGS. 9a-b) that can monitor insulin flow within a delivery tube during each delivery pulse. In the event it is determined that there is no flow 609 (for example, the motor is activated but flow is not detected because of a motor malfunction, air bubbles, occlusion, etc.), the processor/controller can receive a negative feedback and several operation can be performed to enable to distinguish between motor malfunction, air bubbles, and occlusion as will be further explained in relation to FIG. 11. In the event that it is determined that the pump is operating in a normal manner, and thus flow is detected 608 in the delivery tube, the flow detector can measure the flow 610 through the tube, according to some embodiments. The processor/controller 603 can receive a positive feedback and can adjust the flow in the tube based on the measured flow to cause delivery of the insulin (or any other therapeutic fluid) in the tube at a substantially pre-determined flow rate. In some embodiments, the flow can be a pulsatile and the flow detector can detect the flow in each delivery pulse.

To illustrate feedback control operation as described herein, consider the following examples:

1) A bolus of 5.0 insulin units (5 U) is programmed (e.g., at 602 of the procedure depicted in FIG. 10) by the user. The processor 603 controls 604 (e.g., by sending commands) the motor to cause it to operate until 5.0 units is delivered. The flow detector measures delivery of 4.5 U (at 610), and the processor receives the message that 4.5 U were delivered and controls the motor to deliver an additional 0.5 units (achieving the programmed 5 U required dose, 4.5 U+0.5 U=5 U).

2) In another example, a bolus of 5.0 insulin units is programmed (e.g., at 602) by the user, and the processor controls the motor 604 (e.g., at 604 of the procedure depicted in FIG. 10) to operate until 5.0 units are delivered. The flow detector determined a measured delivery of 5.0 U (e.g., at 610) during motor operation, and the processor receives the message that 5.0 U has been delivered and causes immediate stoppage of motor operation.

3) In a further example, a basal rate of 1.0 unit/hour (1.0 U/h) is programmed (e.g., at 602) by the patient. The patch unit administers (motor operation at each delivery pulse) the 1.0 U/h basal dose at 3 minutes delivery intervals (i.e. a quantum is delivered every 3 minutes, 20 per hour) at volume of 0.05 U per motor operation (0.05 U×20/h=1.0 U/h). In this example, assume that the measured flow (performed at 610) at one motor operation is determined to be 0.04 U. The processor receives delivery input of 0.04 U and controls the motor (e.g., by communication appropriate control commands/signals) to administer an additional 0.01 U (0.01 U+0.04 U=0.05 U). If such an adjustment is made in all motor strokes every 3 minutes for an hour (precise delivery of 0.05 U every 3 minutes) the total amount of insulin units (1.0 U) is delivered at 1 hour achieving basal delivery of 1.0 U/h at extremely high precision.

4) In another example, programmed basal delivery rate is 1 U/h (administered at 0.05 U every 3 minutes). At one motor operation (delivery pulse) the delivered dose (measured by the flow detector) is 0.06 U instead of 0.05 U. The processor receives a signal or message from the flow detector representative of the measured flow/dose, and controls the motor to deliver 0.04 U in the next consecutive operation to counterbalance the over delivery (of 0.01 U) of the previous motor operation.

In embodiments where the flow detector is used only for determining a condition of no flow, no further quantitative evaluation may need to be carried out and the flow detector can serve as a binary sensor. In embodiments where motor operation is adjusted based on flow measurements, quantitative evaluation can be required. Both kind of operation may be used either alternatively or in combination.

Figure 11:
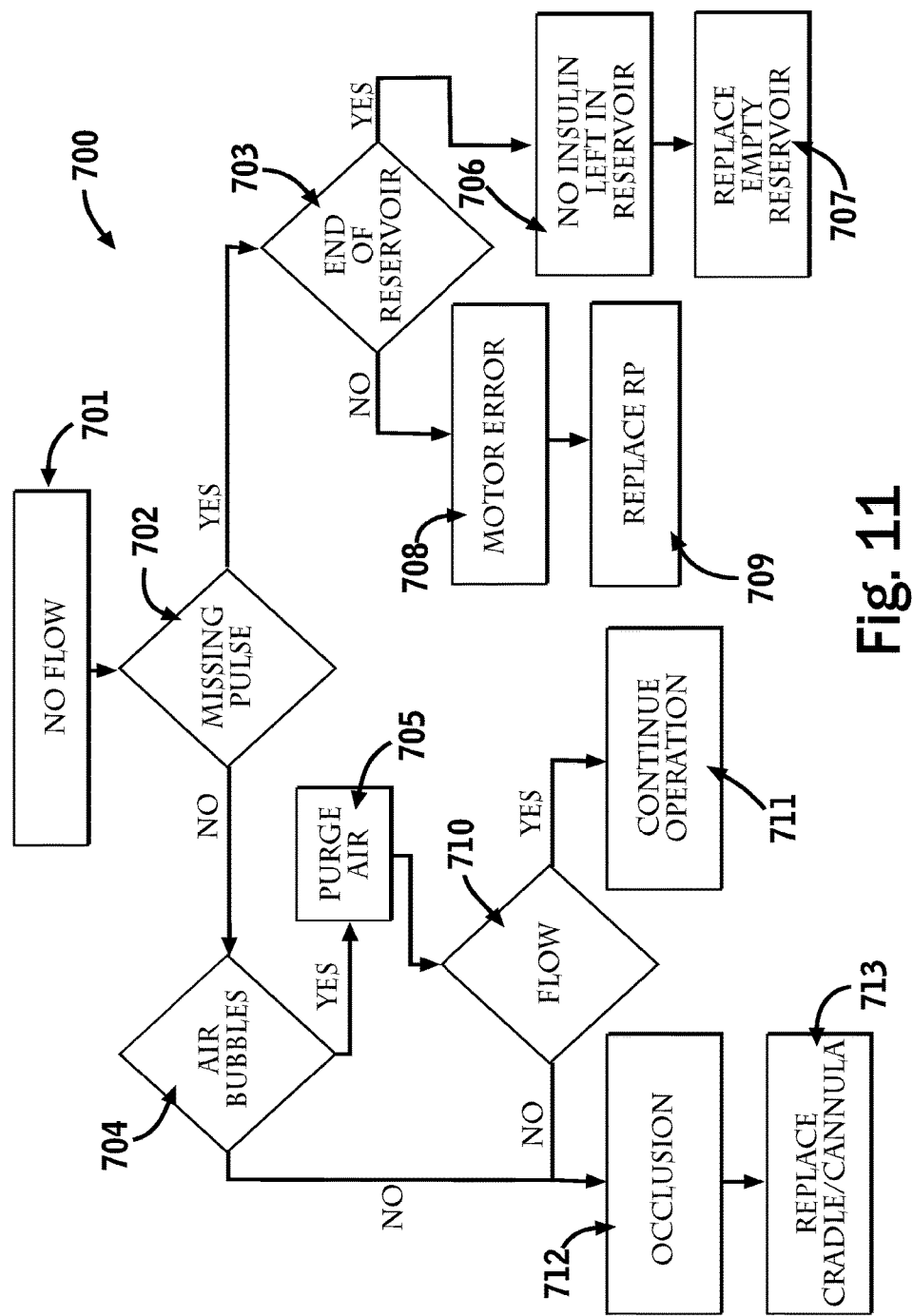
FIG. 11 illustrates a flow diagram of an example "no flow" procedure according to an embodiment of the present disclosure.

With reference now to FIG. 11, a flow chart illustrating operation in the event a "no flow" condition is determined (at 701, corresponding to the operations 609 shown in FIG. 10, is shown. A "no flow" condition can be defined as no fluid flow (e.g., insulin is not delivered) within the delivery tube (such as the tube 230 in FIGS. 8 and 9). This condition can happen in, for example, any one or more of the following four situations: 1) empty reservoir (i.e., no insulin remaining in reservoir), 2) motor or gear malfunction (stuck or broken gear, a motor error, etc.), 3) occlusion (within the delivery tube, cannula, or at any place in the delivery path, and 4) air bubble/s (air can enter reservoir during filling or pump operation and can occupy a major portion of delivery tube). Thus, in the event that no flow is detected by the flow detector at 701, a set of operations can be performed. Particularly, a determination 702 can be performed as to whether there is a missing pulse. A missing pulse can be defined as a mismatch between number of pulses supplied to the motor and the extent (or angle) of revolutions (or number of executed motor steps).

For example, a stepper motor may provide 18° of revolution for each pulse. Therefore, for a pulse train of 10 pulses motor revolution should be 180°, if motor revolution is less than 180° (e.g., 160°), it can follow that some pulses were missed (for example, electrical power was not converted to motor revolution). Motor revolution can be detected by a revolution counter, such as the one shown and described in relation to FIG. 8. As noted, a situation of missing pulses can occur, for example, as a result of an occlusion, a motor/gear error or because of an empty reservoir (determined, for example, based on when the piston reaches the "end-of-motion" point). Empty reservoir may also be detected by the controller/processor using an end of reservoir sensor signal or by direct observation of reservoir by the patient. If the reservoir is determined to be empty, and thus it can be determined 706 that no insulin is left in reservoir, the user should replace 707 the empty reservoir after receiving a corresponding alarm or alert. If it is determined that the reservoir is not empty (because insulin is left in reservoir, as may be determined at 703), it can be determined 708 that a motor/gear error 708 has occurred (e.g., due to motor malfunction, broken gear, etc.). To remedy a determination of a motor/gear error, in some embodiments, the reusable part (comprising motor and gear) may be replaced 709.

If it is determined (e.g., at 701) that there is no flow and it is further determined that there are no missing pulses (e.g., at 702), a determination can be made 704 to confirm or exclude the presence of air bubbles. For example, the patient may visually inspect the device to determine if there are air bubbles (e.g., upon being prompted a "check reservoir" alert). A corresponding instruction may be provided to the patient for example via screen 41 of remote control unit 40. If no air bubbles are detected by the user through direct observation, an occlusion can be determined 712 to have occurred, thus prompting 713 an alert/notice that the cannula and/or cradle may need to be replaced (e.g., the infusion site may need to be changed and a new cradle/cannula set may need to be installed). On the other hand, if it is determined that there are air bubbles in the system, air purging may need to be performed 705, and the pump may need to subsequently be re-operated.

Upon air purging, another determination can be made 710 by the flow detector to determine if fluid flow can be detected. If there is flow (as indicated by the label "yes" near decision block 710), normal operation may be resumed 711. If it is determined by the flow detector (at 710) that even after the purging there is still no flow (as indicate\d by flow-"no" near decision block 710), an occlusion can be determined 712 to have occurred and the cannula and/or cradle may need to be replaced 713. Observation of reservoir status (remaining insulin) can be done after disconnection of patch unit from cradle and upon direct inspection of reservoir. After inspection, the patch unit can be reconnected to cradle and operation may be resumed.

FIG. 12 is a decision table summarizing the various conditions causing no-flow. The table lists four situations that may have resulted in "no flow," and their various indicia (i.e., the various checks and determinations based upon which the condition in question may be identified. In the first situation, the condition of occlusion can be determined to have been detected (i.e., to have occurred) when no flow is detected, but—there is no missing pulse, and there is insulin that remains in reservoir (i.e., the reservoir is not empty). A suitable remedial action when occlusion is determined to have been detected is to replace the cradle and cannula and have the patch unit (the replaceable part (RP) and the disposable part (DP) that can include the reservoir with some remaining insulin) reconnected to a new cradle and cannula. In the second situation, the occurrence of air bubbles can be determined to have been detected when there is no flow, there are no missing pulses, insulin remains in reservoir, and an inspection of air bubbles in reservoir enable the identification of air bubbles. Under those circumstances, a suitable remedial action can include purging air and continuing normal insulin dispensing operation.

In a third situation, a determination that no insulin remains can be made when a missing pulse is detected and an end-of-reservoir condition is detected (e.g., detected using a sensor and/or through a visual inspection). Under these circumstances, suitable remedial action may include replacing the disposable (DP) that contains the reservoir, pairing the DP with a new filled reservoir, connecting the patch unit (with the paired DP-RP) to the cradle, and resuming operation. In the fourth situation listed in the Table of FIG. 12, a motor error can be determined to have been detected when a missing pulse is detected and it is determined that insulin remains in the reservoir. Under these circumstances, suitable remedial actions can include replacing the reusable part (the disposable part with insulin, the cradle, and the cannula do not necessarily need to be replaced).

Figure 13A:
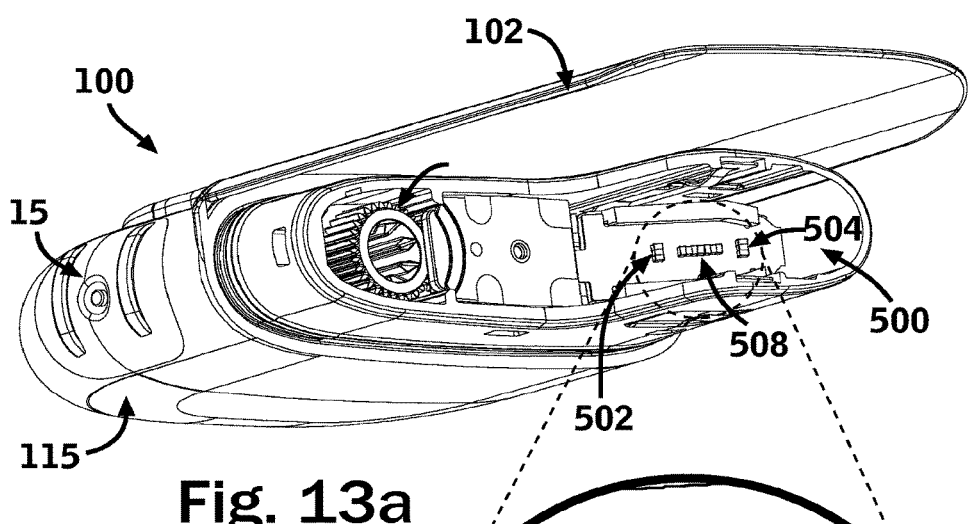
FIGS. 13a-b illustrate a perspective view of the reusable part and a magnified view of the flow detector according to an embodiment of the present disclosure.
Figure 13B:
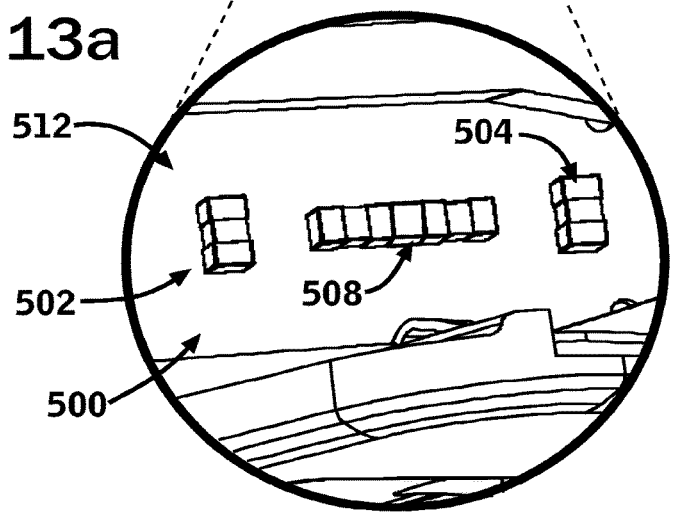

With reference now to FIGS. 13a-b, perspective view of the reusable part 100 (shown in FIG. 13a) and a magnified view of the flow detector 500 (in FIG. 13b) are shown. The reusable part 100 can comprise a reusable part housing 115, a protective shield 102, and one or more optional operating buttons 15. In some embodiments, the flow detector 500 can be an extension of the Printed Circuit Board (PCB) 512 which may serve as a base for a heating element (or "heater") 508 and one or more (e.g., two) temperature sensors 502 and 504. The extension of the PCB can be part of the detector or, in other embodiments, the extension of the PCB can be a separate component to which the detector can be coupled.

In the embodiment shown in FIG. 13 as well as following figures, the temperature sensors 502, 504 can be arranged such that their longitudinal axis can be substantially parallel and can be substantially perpendicular to a longitudinal axis of the heating element 508. In alternative embodiments, the arrangement can be different. In those embodiments, any or all of the heating element 508 and the temperature sensors 502, 504 may be rotated, for example by 90° as compared to the shown configuration. Those configuration changes can particularly influence the sensitivity of the flow detector.

As temperature sensors 502, 504, thermistors may be used in the shown embodiment as well as in embodiments discussed further above and below. Other elements, such as silicone diodes, Schottky diodes, or thermo couplers may be used as well as temperature sensors.

For different reasons, in some embodiments, the heating of the therapeutic fluid can be as low as possible in accordance with the required performance of the flow detector. One reason can be the general demand for low energy consumption. A further reason can be the susceptibility of typical drugs, such as insulin, to heating. Favorably, the temperature raise in the fluid can be below 1 Kelvin and may be, for example, in a range of some $1/1000$ Kelvin.

Figure 14:
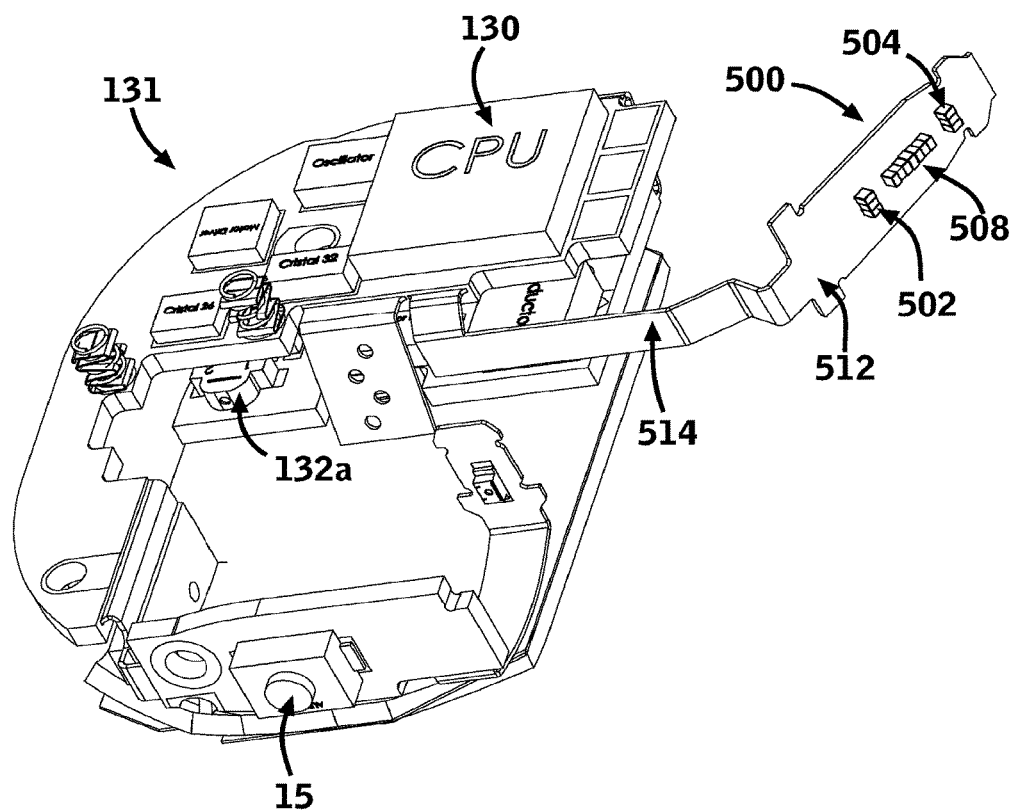
FIG. 14 illustrates a diagram showing a folded PCB within a reusable part and electronic components according to an embodiment of the present disclosure.

FIG. 14 shows the folded PCB 131 and electronic components. The PCB 131 can be a rigid/flexible type with extensions to relevant components. The folded PCB 131 can be contained, in some embodiments, within the RP housing. The PCB 131 can comprise a processor 130, one or more operating buttons 15, a light emitting source (LED) 132a, a light detector 132b (as shown, for example, in FIG. 8) and an extension 514 and 512 that can include the electronic components of flow detector 500. The base of the flow detector 512 (e.g., the PCB extension) can include a heating element 508 and two temperature sensors 502 and 504.

Figure 15:
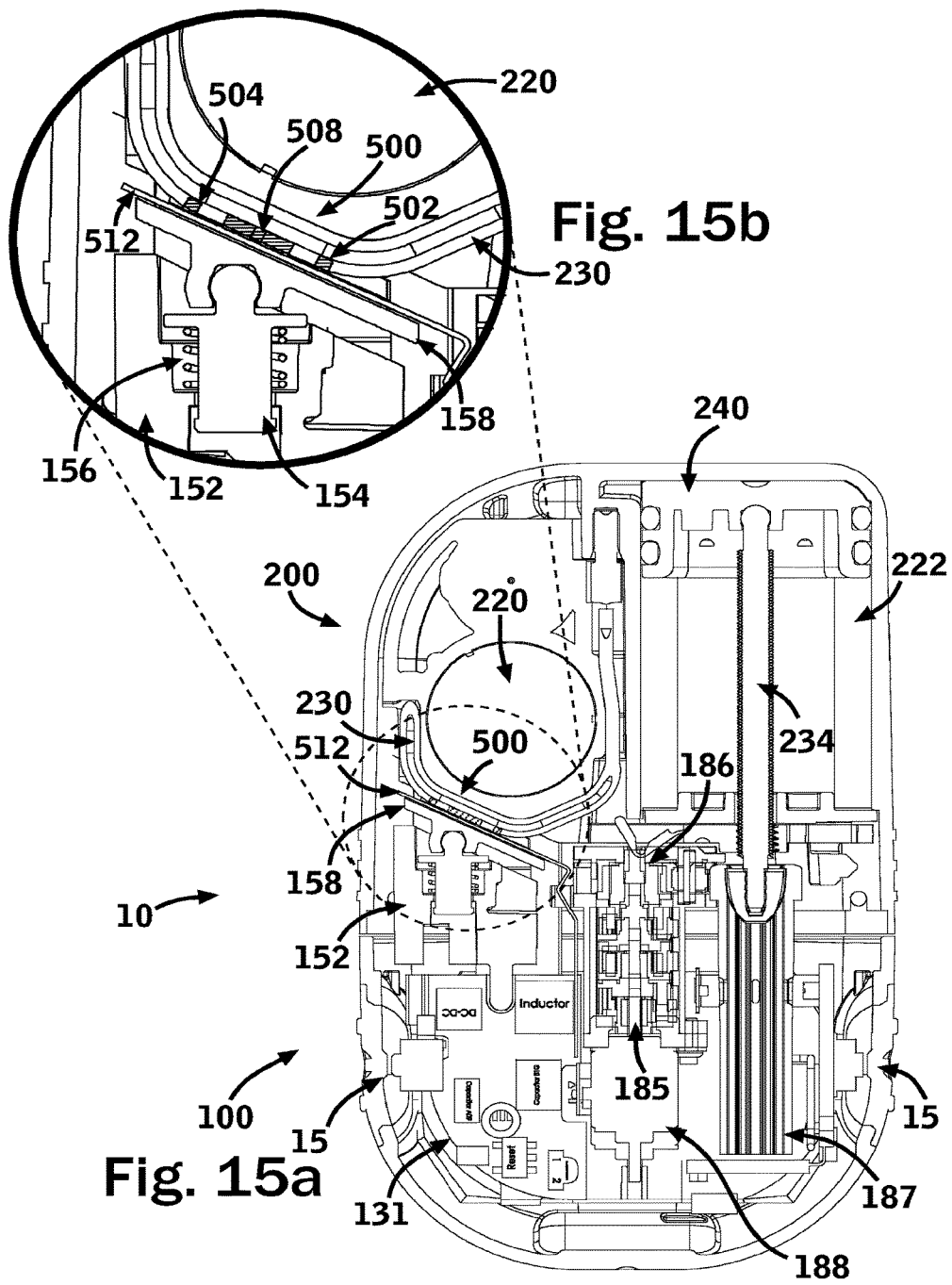
FIGS. 15a-b illustrate a longitudinal cross-sectional view of a patch unit and a magnified view of a flow detector according to an embodiment of the present disclosure.

FIGS. 15a-b show a longitudinal cross section view (FIG. 15a) of the drug dispensing unit 10 and a magnified view (FIG. 15b) of the flow detector 500. In the example shown, the drug dispensing unit 10 can include a reusable part 100 and a disposable part 200. The reusable part can include one or more operation buttons 15, a PCB 131 with an extension that can serve as a base 512 for the flow detector 500, a motor 188 and gears 186 and 187. The gears can comprise a 3-stage reduction planetary unit 185 and additional two spur gear units (rotating sleeve). The disposable part can comprise a reservoir 222, a plunger/piston 240, a drive screw (plunger/piston rod) 234, a delivery tube 230, and a battery 220. The flow detector 500 can thus include the base 512 (PCB extension) as well as a heating element (heater) 508 and two temperature sensors 502 and 504. A flow detector engagement rack (hereinafter "rack") 158 can be connected to the base 512 and may be freely articulated to an engagement rack hub (hereinafter "hub") 154. The hub 154 can be mounted on a spring 156. Upon pairing of the reusable part 100 to the disposable part 200, the DP delivery tube 230 can be placed proximate and, in some embodiments, may come in contact with the heating element 508 and the temperature sensors 502 and 504 mounted on the PCB base 512. The fully articulated rack 158 (also referred to as "alignment rack") can provide alignment of the delivery tube 230 with the heating element 508 and the sensors 502 and 504. The springs 156 can provide a force applied to the hub 154 and the rack 158 against the delivery tube 230 and can close the tolerances gaps during DP-RP pairing.

Figure 16:
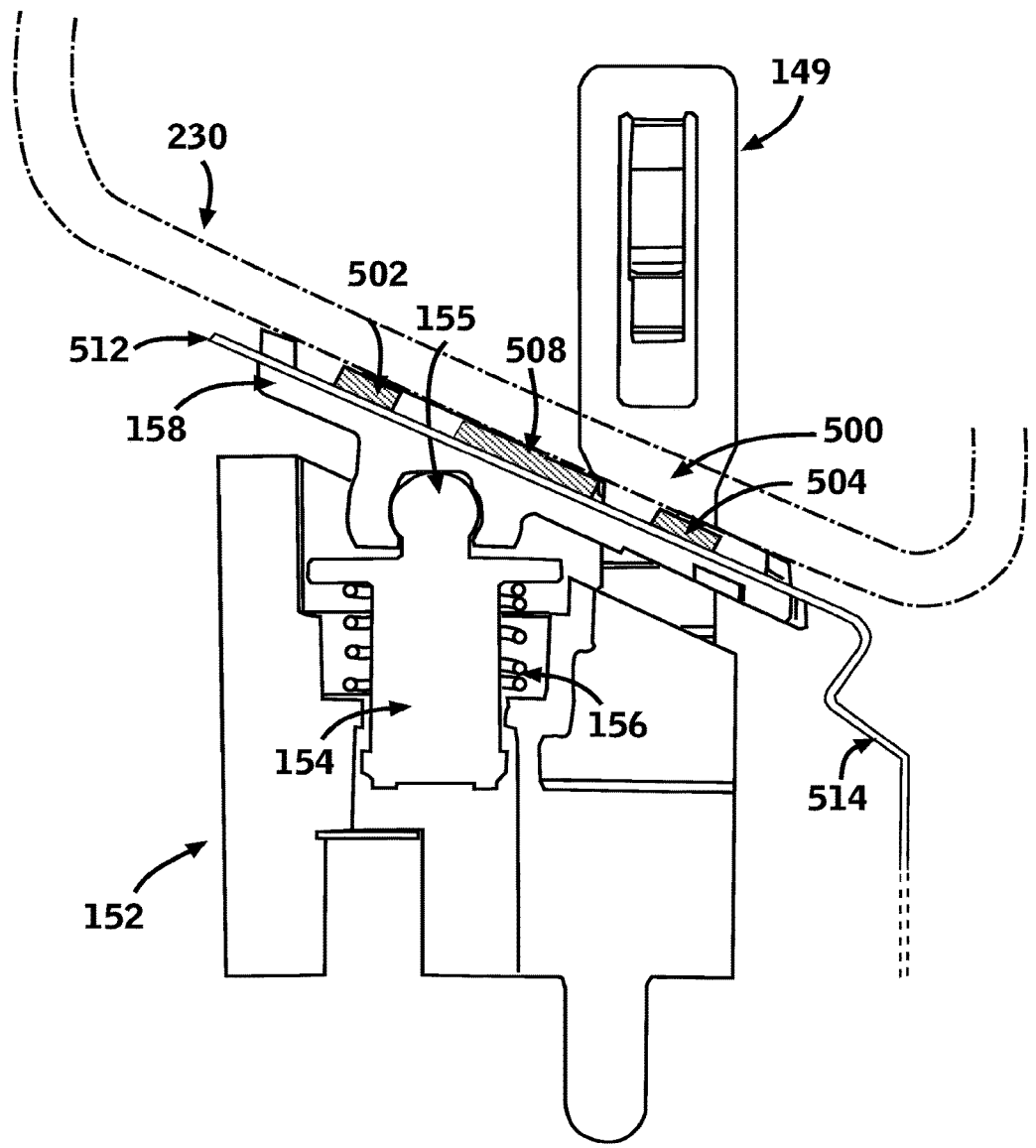
FIG. 16 illustrates a schematic diagram of a flow detector located within a reusable part and engaged with a delivery tube that is located in a disposable part according to an embodiment of the present disclosure.

FIG. 16 is a schematic view of one embodiment, wherein the flow detector 500 located within the reusable part is placed proximate (or comes in contact with) the delivery tube 230 located in the disposable part. The flow detector 500 can comprise, or is otherwise coupled to, a supporting block 152, a hub 154 with a rounded cap 155 (hereinafter "hub cap"), a spring 156, and a flow detector engagement rack 158. In the example, the flow detector 500 can include the PCB extension 514, a PCB base 512, a heating element, and temperature sensors 502 and 504. A battery connector 149 can be positioned in the vicinity of the flow detector 500 and can provide electrical communication between batteries (not shown) located in the disposable part and the PCB electronics located, in some embodiments, in the RP.

Figure 17A:
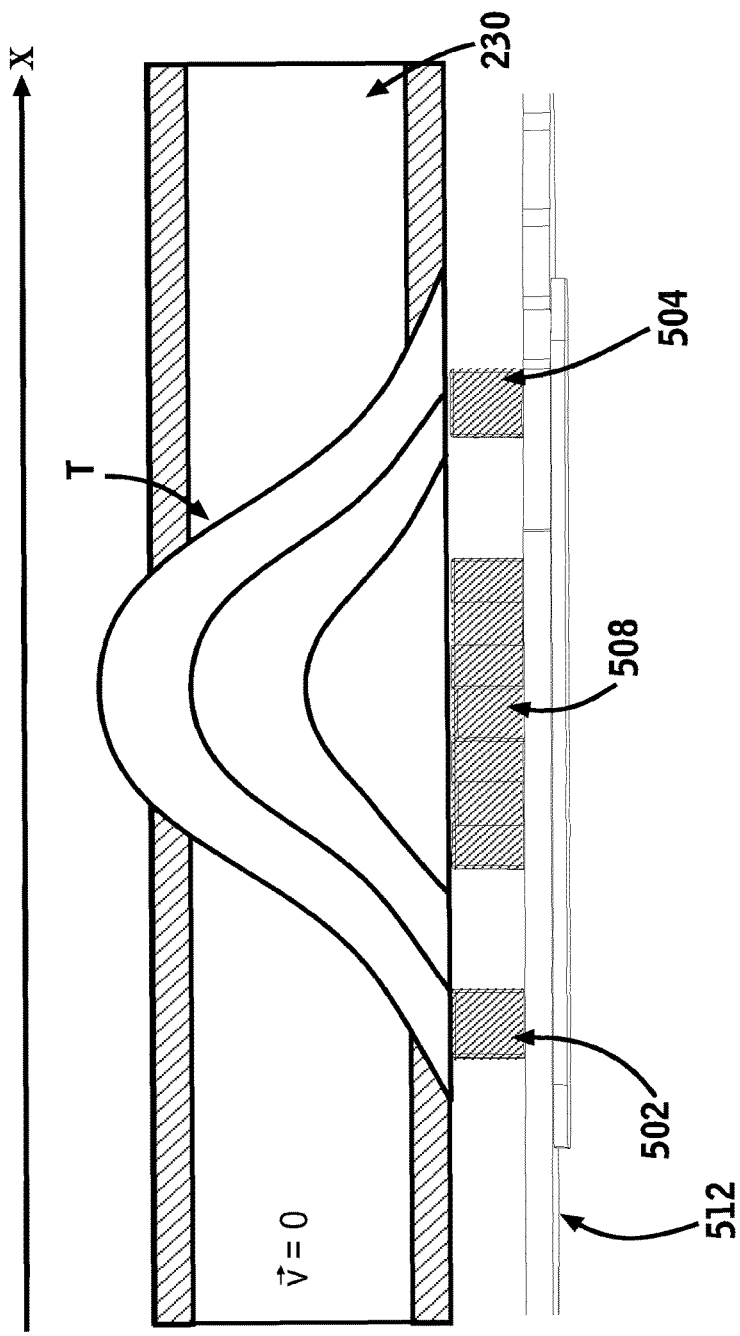
FIGS. 17a-b illustrate schematic diagrams illustrating operation of a flow detector during no flow, and flow conditions according to an embodiment of the present disclosure.
Figure 17B:
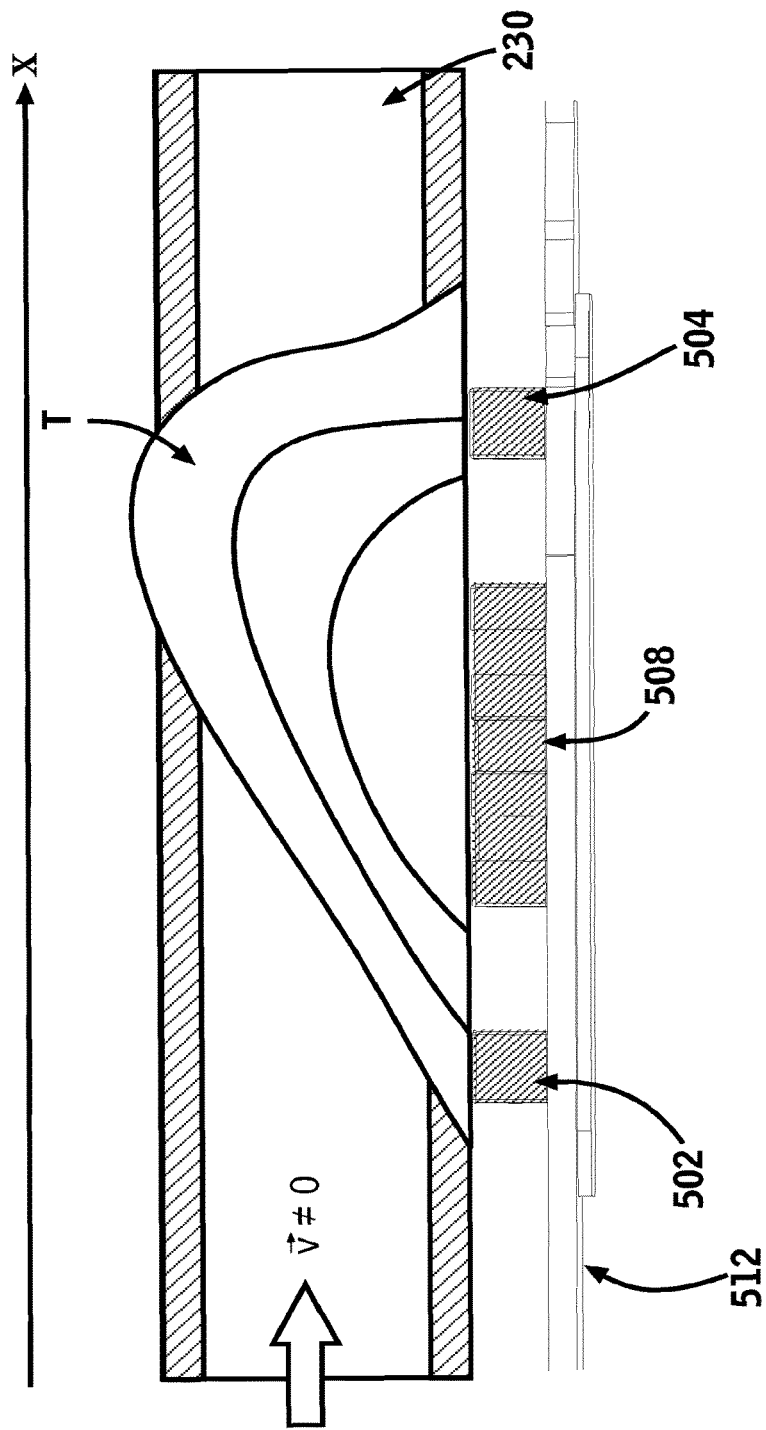

FIGS. 17a-b illustrate the operational principle of the flow detector 500, according to some embodiments, when there is no flow, i.e., V=0 (as illustrated in FIG. 17a) and when there is fluid flow, i.e., V≠0 (as illustrated in FIG. 17b). The heating element 508 and the temperature sensors 502, 504 can be located on the base 512 and can be proximate (and may come in contact with, i.e., touch) the delivery tube 230. The direction of flow (x) is depicted from left to right. In FIG. 17a, where there is no flow (V=0), activation of heating element 508 can cause a temperature rise of the fluid within the delivery tube with substantially symmetrical (e.g., Gaussian) temperature distribution. The curves T can be representative of the temperatures gradient where each line curve is an isotherm (line of equal temperature). In this scenario of no flow, both the temperature sensors 502 and 504 can thus sense the same temperature because the distance between the heating element 508 and the sensor 502 can be substantially equal to the distance between the heating element 508 and the sensor 504. Therefore, an equal temperature detected by both sensors can indicate that there is no flow (V=0).

On the other hand, in FIG. 17b, corresponding to a situation where there is fluid flow within the delivery tube 230 (i.e., V≠0). In this example, flow can be in the direction of x (V>0). Where there is fluid flow in the opposite direction (−x), the flow can be represented as a negative value, i.e., V<0. During operation of the heating element, the temperature gradient can be shifted toward the direction of flow and as a result the isotherms can be skewed (they are not symmetrical). Thus, the downstream sensor (the sensor 504 in this example) can sense a higher temperature than the upstream sensor (the sensor 502 in this example). The temperature differences between the sensors and the rate of change of the temperature difference between the sensors, for example, can be used to determine if fluid actually flows within the tube, and, in some embodiments, to determine the fluid flow rate within the tube. Particularly, because the dimensions of the tube 230, the physical properties of the tube and insulin, and the distance between the heating element 508 and the sensors 502, 504 are all known values, determination of the volume flow rate (which may be represented as Q) can be performed.

Figure 18:
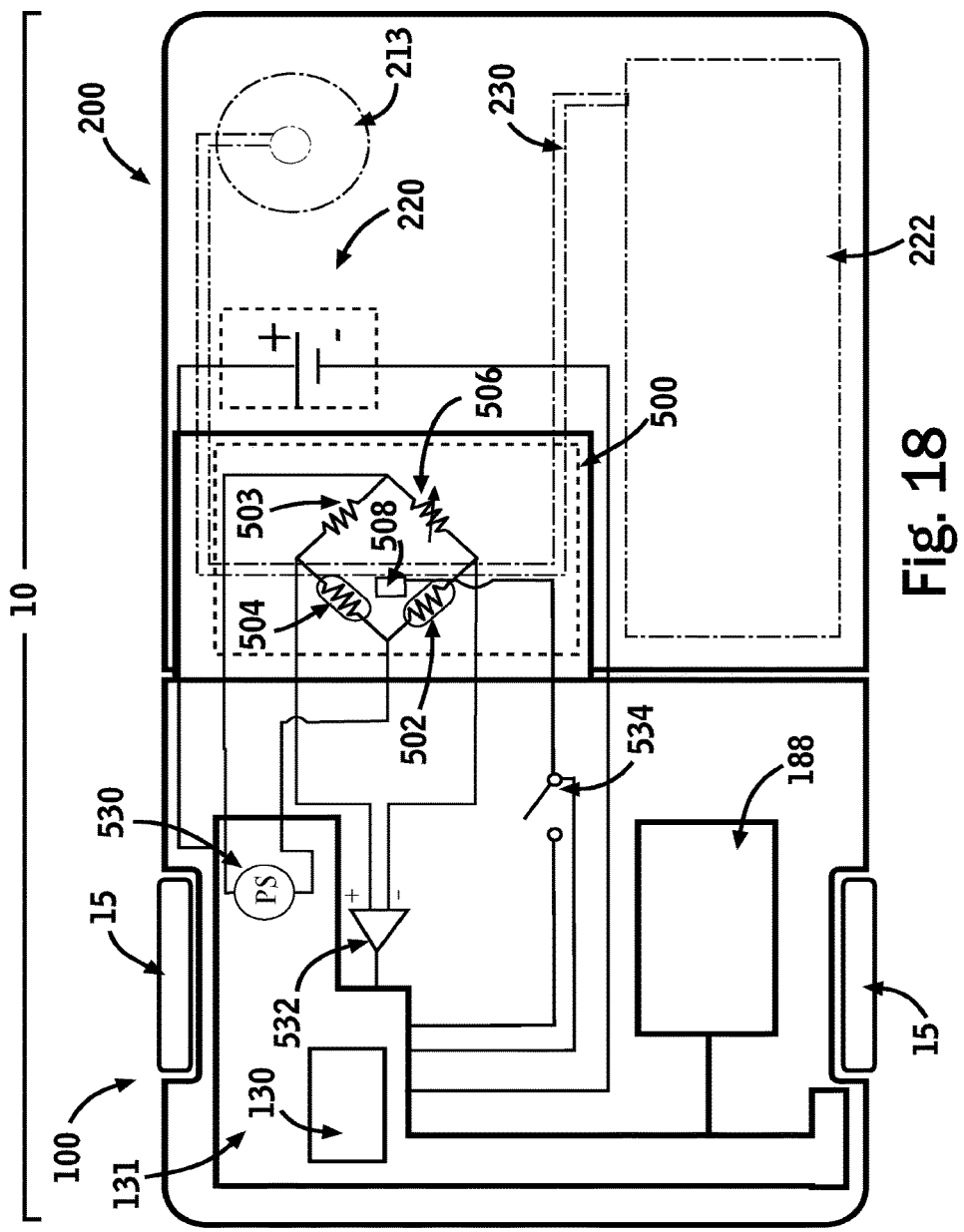
FIG. 18 illustrates a schematic diagram of a flow detector and some of electronic components thereof according to an embodiment of the present disclosure.

FIG. 18 is a schematic diagram with an electrical circuit implementation of the electronic components of the flow detector. The patch unit 10 can include a reusable part 100 and a disposable part 200, both including interlocking housings that maintain sealing after pairing.

The reusable part 100 can have a protruding part that can include the flow detector 500 which can be received in the disposable part housing such that after pairing at least a part of the flow detector 500 can be proximate to, or comes in contact with, the delivery tube 230 of the disposable part 200. The reusable part 100 can include one or more optional operating buttons 15, a motor 188, PCB/electronic components 131 that may include a processor 130, and a flow detector power supply (PS) 530.

The disposable part 200 can include a reservoir 222, a delivery tube 230, a battery 220, and an exit port 213. Power to the PCB/electronics 131 (including to the processor 130) may be supplied from the battery 220 located in the disposable part 200. In some alternative embodiments, one or more batteries can reside in the reusable part 100. In some embodiments, the battery 220 may be a rechargeable battery. The heating element 508 can receive operation commands and/or control signals from a processor-controlled heater driver 534. The driver 534 may be configured to cause power to be provided to the flow detector to operate the sensors and the heating and to enable controlling the heating duration (for example, 30 milliamps for 30 milliseconds).

In some implementations, the two temperature sensors 502 and 504 can be connected to a resistor 503 and a tapped resistor (potentiometer) 506 to form a Wheatstone bridge (used to measure an unknown electrical resistance by balancing two legs of a bridge circuit, one leg of which includes the unknown component). In a variant, resistor 503 can be a tapped resistor (potentiometer), too. The tapped resistor 506 or the tapped resistors 503, 506 may be realized as digital potentiometers with electronically controlled resistance.

A nominal résistance of each of the temperature sensors 502, 504 may, e.g., be about 10 kOhm in an exemplary embodiment. In this embodiment, resistor 503 may have a value of about 3.24 kOhm. The potentiometer 506 may have a resistance that is variable in a range from about 2.68 kOhm to about 3.79 kOhm in this particular example. These values are only examples. Typically, resistance values may range from very low (e.g., about 10 Ohm) to very high (e.g., about 100 mOhm).

The Wheatstone bridge arrangement can receive electrical current from the bridge power supply (e.g., PS 530). As noted, the temperature sensors can be basically tapped resistors that change the resistance according to temperature change.

The Wheatstone bridge can be supplied by power (PS) and the difference in voltage at two bridge points (V-output) may be compared to the supplied voltage (V-input). Accordingly, the resistance of the tapped resistors (resulting from temperature change) in the bridge can be determined to thus enable derivation of the temperature gradient. In some embodiments, the temperature sensors can be thermo-resistors (also called thermistors or temperature dependent resistors). Other suitable temperature sensors can include thermocouples and thermo-elements based on Seebeck and Peltier effects and semiconductor devices including of P-N junctions that can have a temperature-dependent current rate, or Schottky The Wheatstone bridge output signal (voltage difference) can be determined by the changes of resistance values in the bridge. A differential amplifier 532 can amplify the bridge output signals that are then processed by, for example, the processor 130.

Figure 19:
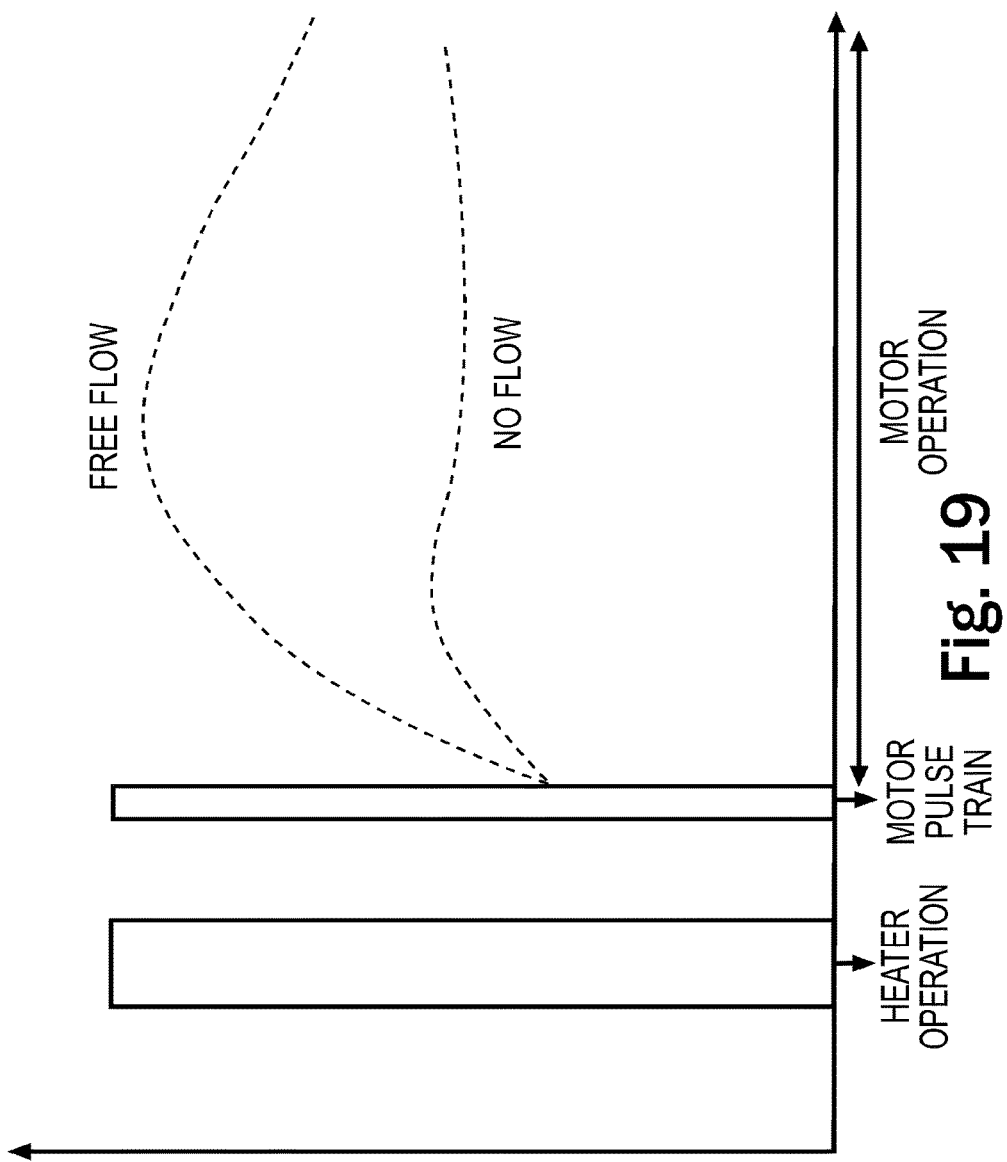
FIG. 19 illustrates a graph illustrating a heating element/motor sequence of operations and flow patterns in the cases of flow and no flow within the delivery tube according to an embodiment of the present disclosure.

FIG. 19 is a schematic view illustrating motor/heater sequential operation and flow patterns in the cases when there is fluid flow and when there is no fluid flow within the delivery tube. The X axis can denote time and the Y axis can denotes the flow "pattern". When there is "no flow", there can be no significant changes regarding the temperature gradient or the flow rate. When there is "free flow", there can be variations to be detected (the fluid first accelerates because of the pulse given by the motor). Due to high energy consumption of the motor and the heating element (heater), in some implementations, the heating element can be operated (to cause fluid warming) before motor operation begins in accordance with some predetermined time sequence. Heating timing and duration (in milliseconds) and motor operation timing and duration may also be pre-determined. Thus, by the time the motor is operated, a temperature gradient can have already been established and flow movement can shift isotherms to a skewed shape as shown, for example, in FIG. 17b. The two curves in FIG. 19 show a typical flow versus time patterns in cases of "no flow" and "free flow" conditions. Motor operation can drive fluid from the reservoir through the delivery tube and the flow detector determines/measures flow by integrating the differences between the temperature sensors (e.g., V-output in the implementation of FIG. 18) during a predefined measurement period (for example, several seconds, e.g., 1-2 seconds) at a pre-determined number of measurements (for example, between 2-1000 times during the measurement period) The integral (area under the time/flow curve during predetermined time) may then be computed. Operation of the heating element followed by motor operation and a predefined measurement period can be referred to as a "measurement cycle." Alternatively or additionally, the slope of a temperature (or temperature gradient)-versus-time curve can be evaluated as will be discussed further below in more detail.

The evaluation can thus be used for either or more of the following purposes: Flow measurement—the volume of fluid emerging from the reservoir at each motor operation and/or at predefined number of motor operations (e.g., 10 consecutive operations) and/or at predefined operation times (e.g., total motor operations during a 1 hour period) can be measured. Flow measured by the flow detector can be used to calibrate the pump (calculating the ratio of motor cycles and volume of expelled fluid, i.e., the K value) during priming. Calibration of the pump may otherwise be carried out at the manufacturing facility, or periodically, e.g., according to a predetermined time schedule. Calibration of the flow detector can be done in the manufacturing facility by comparing flow measured by the flow detector to the actual flow (measured, for example, by a gravimetric procedure, i.e., weight of expelled volume).

Leakage detection—in the event of a downstream leakage (leakage in the delivery path occurring after the contact point between the delivery tube and the flow detector), the pattern of time/flow curve can change. The change can be related to reduce resistance which can result in a flow pattern change. The patient can receive a notification on possible leakage and can take appropriate remedial actions, for example, performing an inspection of the infusion site.

To illustrate uses of the above described measurement procedure (including computing the time/flow integral), consider the following examples.

As noted, in some implementations, the procedure may be used to perform quantitative flow measurement. For example: The fluid can be rapid acting insulin (100 units/mL of insulin analogs Aspart, Lispro, or Glulisine), The pump can be preset at basal rate of—1 U/h Motor operation mode preset—0.05 U every 3 minutes (20 operations/h=1 U/h)

Flow detector measured volume at each motor operation is 0.5 mm$^3$ or 0.05 U and total volume during a 1 hour period (20 motor operations×0.05 U) is 1 U.

This value can be used by the controller/processor to adjust the programmed value, as illustrated, for example, in FIG. 10. For example, if the programmed value (in this case basal rate) is 1 U/h and the calculated integral value is 0.9 U/h, the controller/processor can send a control command to the motor to cause it to deliver an additional 0.1 U (0.9 U+0.1 U=1.0 U).

As noted, in some implementations, the procedure may be used to facilitate calibration in a manufacturing facility. For example, during a one (1) motor cycle (20 pulses×18°/pulse=360°), the gravimetric measurement can be determined to be 1 U, while the flow volume measured by the flow detector is 0.9 U. Accordingly, the flow detector may be reset so that the flow detector's measurement value is corrected to 1 U/cycle.

In some implementations, the procedure may be used to perform calibration during priming. For example, priming may be preset to 1 U (after the DP-RP pairing and air purging, motor can be operated and insulin can drip from the exit port) and the flow detector can measure 0.9 U. In this case, the controller (processor) may reset the K value (ratio between the motor cycle and expelled volume) such that a desired insulin volume of 1 U can match the actual delivered 1 U.

As noted, the systems, devices, and methods described herein may be used to enable occlusion detection. For example, a predefined value of the time/flow curve integral can be used as a cutoff value to determine whether there is occlusion (i.e., perform a Yes/No occlusion decision). Calibration of the flow detector (defining the cutoff value) can be done during priming. After a few motor rotations (allowing compensation for system loading), the processor can compute the area under the time/flow curve during no occlusion condition. This value (minus a predefined cushion) can serve as a cutoff value (occlusion threshold) for "no occlusion". This procedure can be repeated more than one time (e.g., 3-10) and the average value may be used as the selected cutoff/threshold value. Motor rotation can be monitored with a revolution counter (motor cycle encoder) as shown, for example, in FIG. 8, and as described in relation thereto.

In one example, priming can be set to one (1) motor cycle (360° rotation) that can be equal to 1 U (one insulin unit). The cutoff value (occlusion threshold) can be set to 0.8 U. If, during normal operation (insulin is delivered to subcutaneous tissue), after 1 motor cycle the flow detector measures less than 0.8 U, occlusion can be for example deemed to have occurred and the occlusion alarm can be activated.

As noted, detection of "no flow" can mean occlusion, air bubbles, motor error, or end-of-reservoir (empty reservoir). A procedure to identify/distinguish between these conditions is described herein in relation to FIG. 10.

The following are examples of energy saving procedures during various operation modes. For a low basal rate (0-1 U/hour), the motor can be operated at a time interval≥3 minutes for example (i.e., more than 3 minutes between motor operations). The processor may operate a measurement cycle during every motor operation (where every motor operation may be preceded by a heating operation and followed by a measurement cycle).

For a high basal rate (>1.1 U/hour), the motor can be operated at a time interval≤3 minutes for example (i.e., less than 3 minutes between motor operations). In this situation, the processor may operate a measurement cycle only at the last motor operation in the 3 minutes time interval.

For a small bolus (<0.5 U), the motor can be operated every second, for example. In this situation, the processor can operate a measurement cycle at the first and last motor operations.

For a large bolus (>0.5 U), the motor can be operated every second for example. In this situation, the processor can operate a measurement cycle at the first, middle and last motor operations (e.g., bolus 5 U, measurement cycle at 1$^{st}$ motor operation, after 2.5 U, and at last motor operation).

FIGS. 20*a-b* show a heater and motor activation sequence. In some embodiments, the power supply to power the heating element and the motor may be one or more capacitors (e.g., a battery charges the one or more capacitors and the one or more capacitors discharge the supplied energy to cause motor and heating element operation). FIG. 20*a* shows a typical time sequencing of a heater operation followed by capacitor charging, followed by motor operation, followed by another cycle of capacitor charging. In the event of a pulse train (more than one sequential pulses), one heating element operation can be followed by a sequence of motor operation-capacitor charging.

FIG. 20*b* shows a pattern of voltage (or current) versus time curve over for a capacitor used to power the motor and/or heating element. During the heating operation, the capacitor can be discharged so as to supply current to the load (e.g., the heating element). In this example, the heating time can be 100 milliseconds. Following heating operation, the capacitor can be recharged and the motor can be operated by another cycle of capacitor discharge. In this example, the motor operation can last approximately 20 milliseconds.

Figure 21:
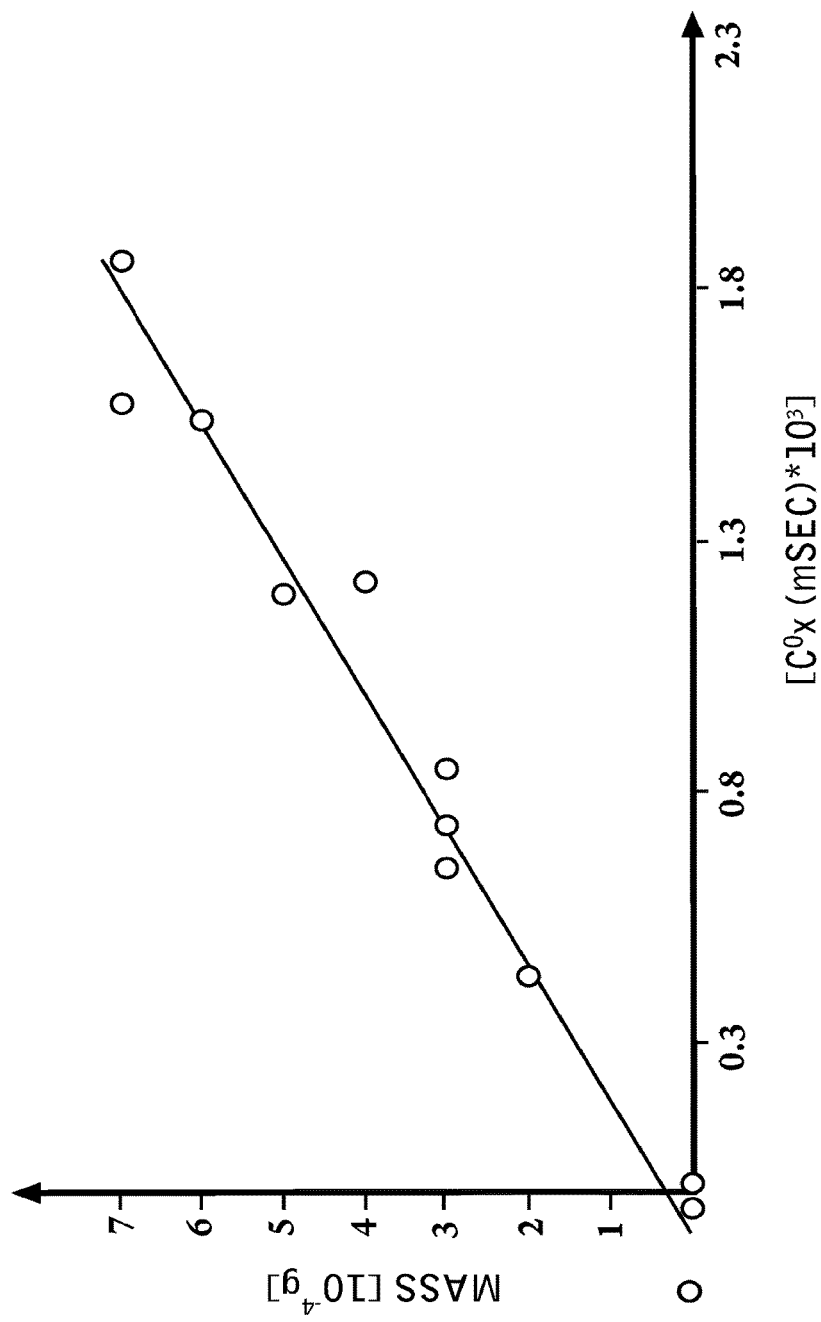
FIG. 21 illustrates a graph showing results of a test comparing volumes (Q) of delivered flow measured with a flow detector and with a gravimetric scale according to an embodiment of the present disclosure.

FIG. 21 is a graph showing the results of experimental tests comparing volumes (Q) of delivered flows. The x-axis can be the flow volume measured with the flow detector and the y-axis—is the flow volume measured by a gravimetric method (e.g., weighted volume of expelled fluid with high sensitive scale). As shown in the graph, there can be a correlation or at least a strong agreement between the flow detector measurements (according to the present disclosure) and the scale measurements.

FIG. 22-25 show other examples of a flow detector 800 including four thermistors according to one embodiment (more or less thermistors or temperature sensors can be implemented).

Figure 22:
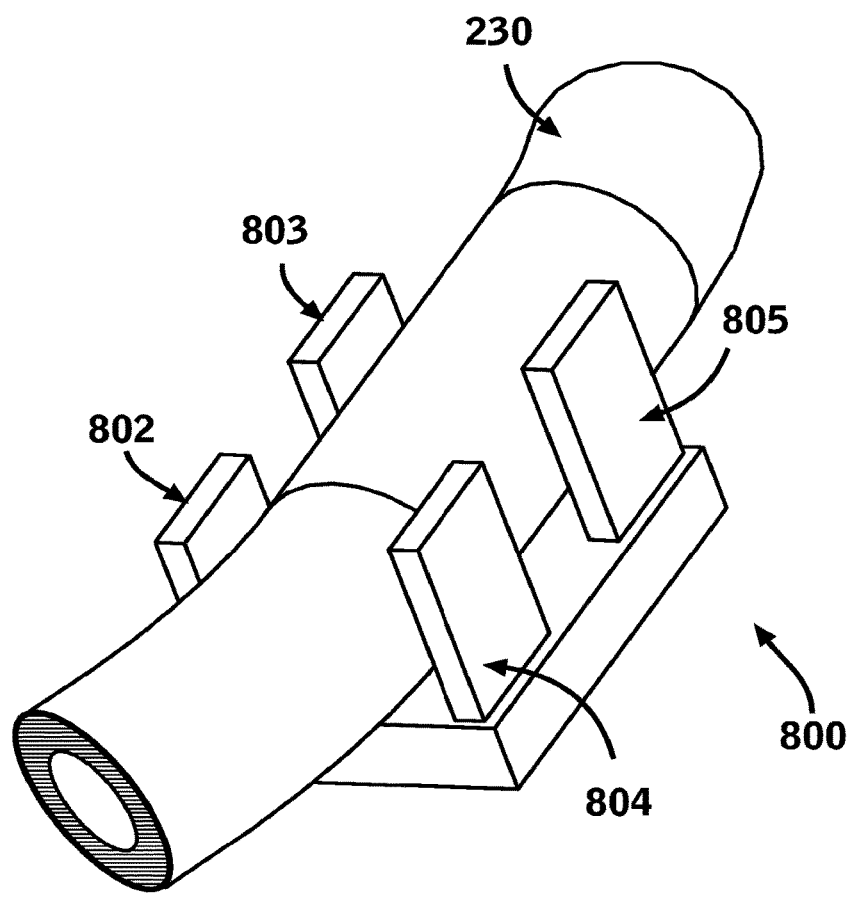
FIG. 22 illustrates a view of an example embodiment of a flow detector with four thermistors, each of which can serve as a heating element or as a temperature sensor according to an embodiment of the present disclosure.
Figure 23:
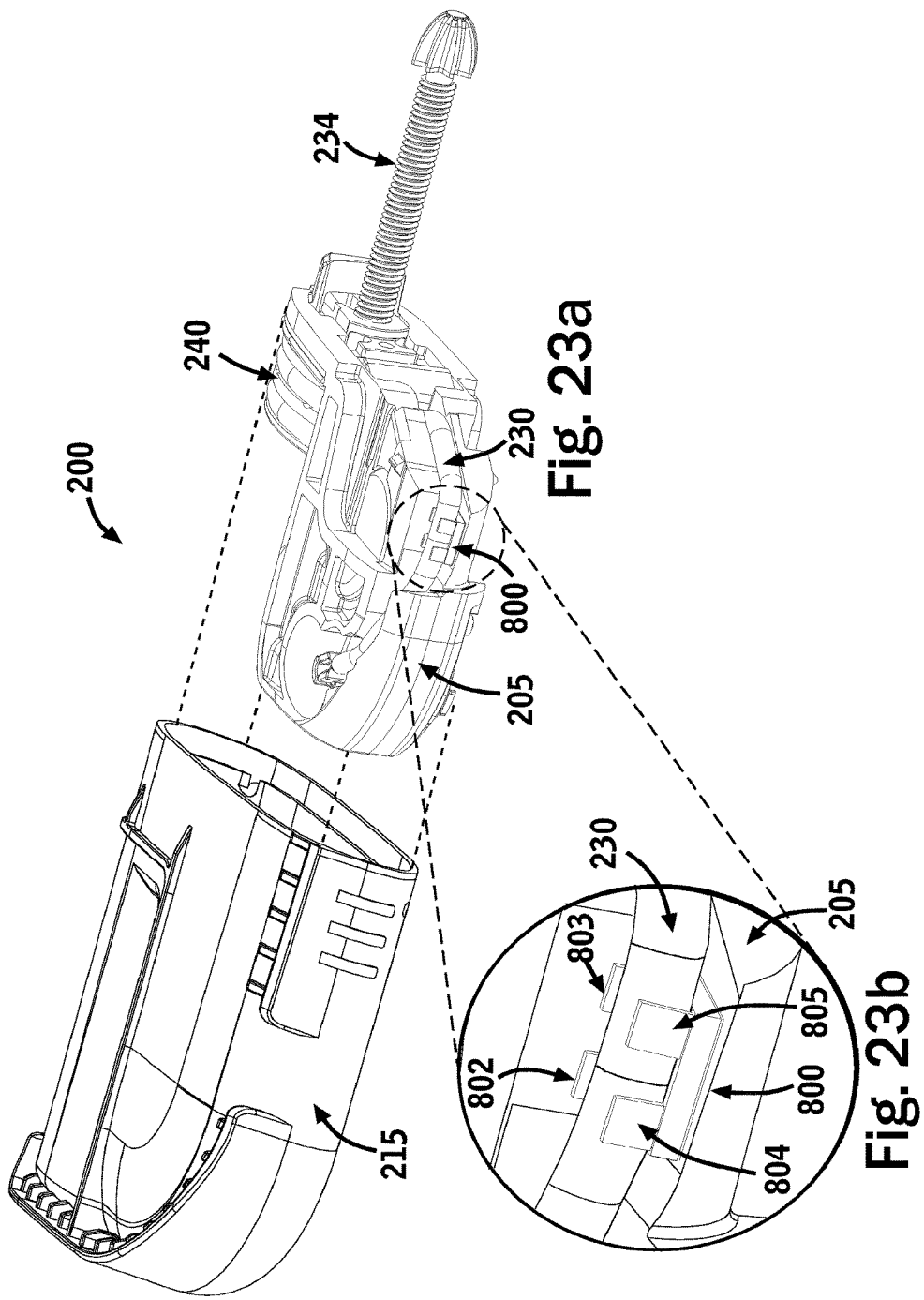
FIGS. 23a-b illustrate views of a disposable part with a flow detector according to an embodiment of the present disclosure.

FIG. 22 shows the four thermistors 802, 803, 804, 805, each of which may serve as a heating element and a temperature sensor. The four thermistors can be in proximity or in contact with the delivery tube 230, thus providing good thermal coupling. According to other embodiments, the thermistors can be mounted, molded, glued, inserted or the like at the proximity and/or in and/or on and/or within the delivery tube. Thermistors of particular shapes (for example curved to spouse the tube) can also be used in order to improve the accuracy of measurements. Particular placements of sensors also can improve measurements.

FIG. 23*a-b* shows one embodiment where the disposable part 200 can include a housing (pocket) 215 and a chassis

205. The chassis can anchor a plunger/piston 240, a drive screw (plunger rod) 234 and a delivery tube 230. FIG. 23*b* shows a magnified view of an example of a flow detector 800 that can detect flow within the delivery tube. In one embodiment, the flow detector 800 can be attached to the chassis of the reusable part and can comprise four thermistors 802, 803, 804, and 805.

Figure 24:
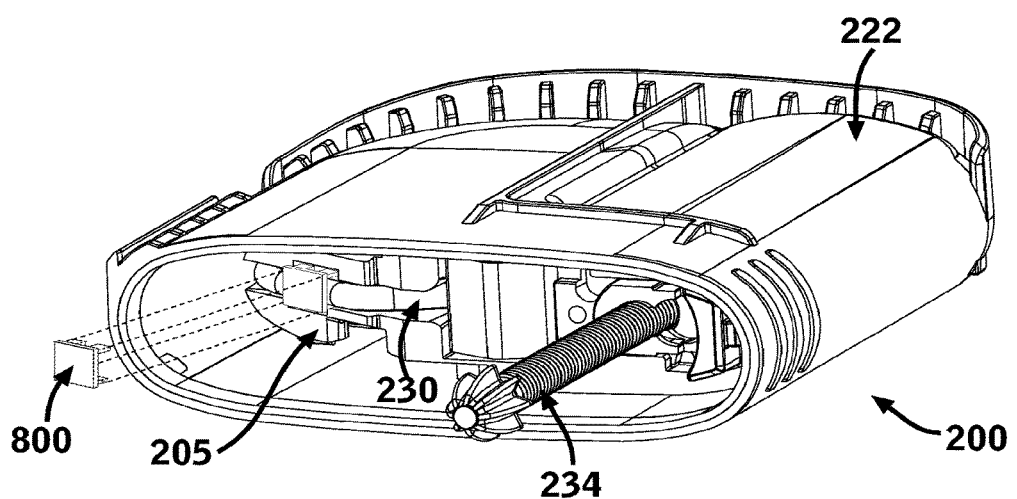
FIG. 24 illustrates a diagram of a disposable part including a flow detector, with the chassis and housing connected according to an embodiment of the present disclosure.

FIG. 24 shows the disposable part 200 that can comprise a reservoir 222, a delivery tube 230, a chassis 205, and a drive screw/piston rod 234. The flow detector 800 can be contained within the reusable part. Upon the pairing of reusable part and disposable part, the flow detector 800 can come in contact with the delivery tube 230.

Figure 25A:
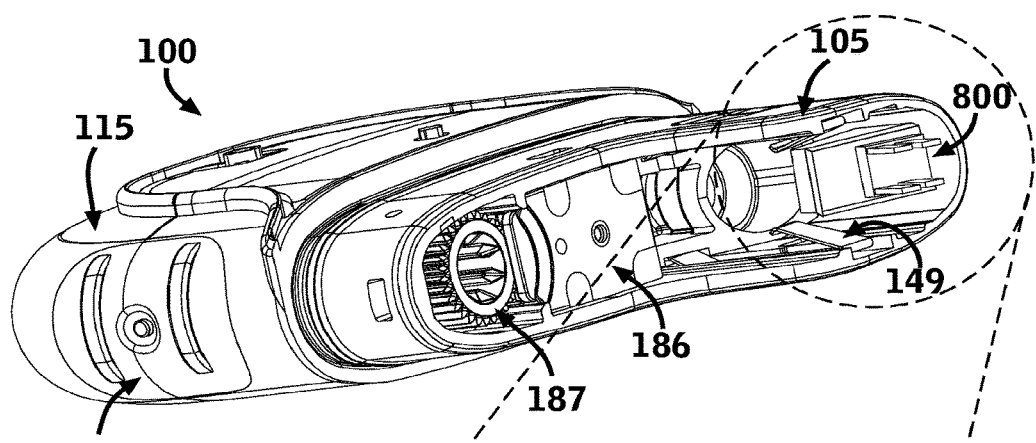
FIGS. 25a-b illustrate a flow detector within a reusable part and a magnified view of the flow detector according to an embodiment of the present disclosure.
Figure 25B:
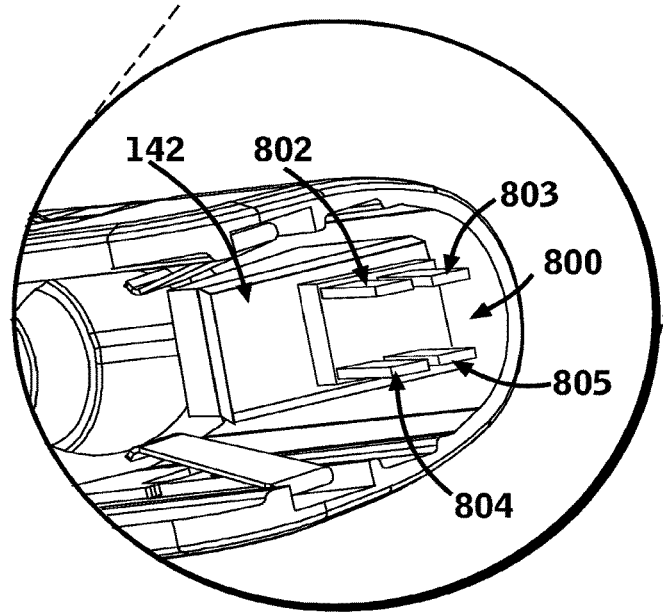

FIG. 25*a-b* shows the reusable part 100 that can comprise a chassis 105, a housing 115, one or more operating buttons 15, battery connectors 149, and gears 186 (planetary) 187 (rotating sleeve). FIG. 25*b* shows a magnified view of flow detector 800 connected to the base 142 and comprising thermistors 802, 803, 804, and 805.

In one embodiment, the temperature sensors can be located in the reusable part. These sensors elements can be rather expensive. The use of the heat coming from the PCB can render this arrangement useful. Nevertheless, in some embodiments, the temperature sensors can be located in the disposable part. According to yet another embodiment, the sensors can be present in both parts (distributed over the two parts, either symmetrically or asymmetrically). The temperature sensors can even be located in a third external part provided the external part can come close or in contact with the tube at one or another placement along the tube (for example, the temperature sensing part can be part of a chip or of a "cartridge" or of an insertable element, adapted to come in contact with the tube when inserted into the pump housing).

In general, several couples (or sequences) of heating element(s) and temperature sensor(s) can be implemented, so that verifications and optimizations can be handled. Different combinations or sequences can be thus be made. For example a "failsafe" arrangement would comprise one heating upstream and two sensors downstream (spaced by a few millimeters for example). The arrangement also can be repeated (one heating element—one sensing element followed by one heating element—one sensing element again).

The fluid (increasing the temperature) can be heated. Cooling the fluid (decreasing the temperature, by heat pump, for example by vapor (de)compression cycles) can provide the same effects and possibilities as described herein. A further (and symmetrical) embodiment can thus comprise in dissipating the heat of the fluid (decreasing the temperature of the fluid) and can measure the temperature distribution according to the same principle described herein.

The fluid circulating in the device can be managed. Data collected by sensors (for example temperature sensors) can be interpreted and the reality of the flow of the fluid in the device can be assessed or controlled.

One or more relationships between the fluid temperature and the fluid flow can be established. Such assessments can enable the control of the fluid flow and in particular can allow an enhanced regulation of the device. The changes in fluid temperatures can be done in an economically way (cheap heating source) or by using existing sources of energy (derivation of energy from the battery for heating) or by re-using already emitted energy (in one example, from the PCB unit). The energy management can be optimized.

In one example of the particular relation of "energy" with "information" (thermodynamics laws) can be illustrated. As disclosed, the arrangement can "re-use" the wasted energy in the device (i.e. the PCB) in order to enable the operation of a sensing circuit (information), leading in turn to a better management of the device. This cycle can lead to a saving of more energy. At a certain stage, an optimum/equilibrium can be reached.

Figure 26:
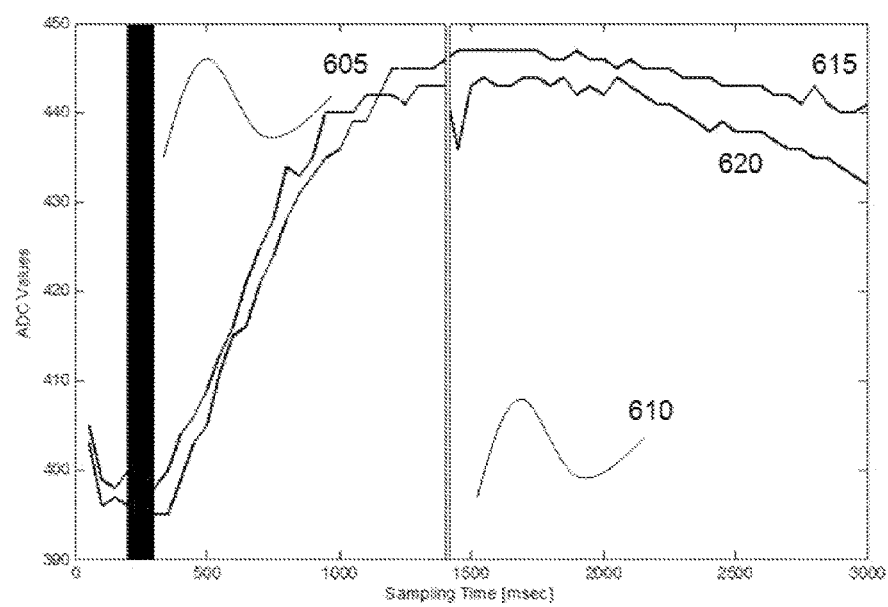
FIG. 26 illustrates a graph of exemplary temperature gradient versus time curves, indicative of a "flow" and a "no flow" condition, respectively according to an embodiment of the present disclosure.

FIG. 26 illustrates a further embodiment of a method for distinguishing between alternative conditions "flow" and "no flow" following motor operation. The method may be implemented in a fluid delivery device, e.g. by corresponding firmware code executed by processor 130.

The two curves 615, 620 as shown in FIG. 26 can each represent a temperature gradient, given by a temperature difference between the temperatures as measured by flow sensors, 502, and 504 over time. The temperature difference can be expressed in Analogue-to-Digital (ADC) converter values. Curve 615 can represent the "now flow" condition while curve 620 can show the "flow" condition. The flow detector design may be designed as discussed above with reference to FIG. 13 and following. This design can be assumed in the following for exemplary purposes.

At the beginning, some offset can be present which can be design-given and may be adjusted by electric calibration via tapped resistor 506 or tapped resistors 503, 506 in general accordance with FIG. 18. The offset may be selected such that that the dynamic range of the analogue/to digital converters can be approximately maximum. Upon a heating phase 605 in which heating element 508 is activated, the fluid temperature can increase. Since no flow is present at this point in time, the temperature distribution along the delivery tube can generally follows FIG. 17*a* as discussed above. Due to some design-given asymmetry of flow detector 500, in particular somewhat different thermal environments for the temperature sensors 502, 504 (as determined, e.g., by surrounding housing components, further electronic components, and copper-based conductive paths), the temperature gradients can increase.

After an exemplary time delay of about 1 second, the motor can be operated. In the case of flow, the heated fluid in the delivery tube in the area of flow detector 500 can be delivered to the exit port and substituted by following non-heated fluid, resulting in the temperature gradient decreasing, curve 620. In the case of "no flow", in contrast, the heated fluid in the area of the flow detector 500 cannot be substituted by following non-heated fluid. Accordingly, the temperature gradient can decrease only slowly as heat is lead away via thermal conductivity and/or radiation, curve 615. It can be seen that the slope of curve 615 can be significantly smaller as compared to curve 200.

Therefore, the slope of the temperature gradient as function of time may be used for distinguishing between "flow" and "no flow" conditions, e.g., by comparing a numerically computed slope value with a threshold slope. Slope computation can be carried out using two or any larger number of samples and generally known numerical algorithms. A portable therapeutic fluid delivery device with a flow detector can comprise a heating element and two temperature sensors. Upon activation of the heating element, a flow condition of the fluid inside the delivery tube can be determined based on a signal provided by the temperature sensors. A temperature gradient within the therapeutic fluid can be detected. The determined flow condition can be one of: air bubbles within the delivery tube, occlusion within the delivery tube, or leakage within the delivery tube. The device can be in two parts, for example with a reusable and a disposable part. Upon the pairing of these parts, the heating element and the temperature sensors can touch the delivery tube. Other embodiments relate to alarms, integration of a blood glucose sensing apparatus, occlusion detection, suspension of motor power, analysis of motor revolutions, and use of a plurality of sensors.

Various features and functions of embodiments may be realized in digital electronic circuitry, integrated circuitry, specially designed ASICs (application specific integrated circuits), computer hardware, firmware, software, and/or combinations thereof. These various embodiments may include one or more computer programs that can be executable and/or interpretable on a programmable system including at least one programmable processor, such as a micro controller, which may be special or general purpose, coupled to receive data and instructions from, and to transmit data and instructions to, a storage system, at least one input device, and at least one output device. Some embodiments can include specific "modules" which may be implemented as digital electronic circuitry, integrated circuitry, specially designed ASICs (application specific integrated circuits), computer hardware, firmware, software, and/or combinations thereof.

These computer programs (also known as programs, software, software applications or code) can include machine instructions for a programmable processor, and may be implemented in a high-level procedural and/or object-oriented programming language, and/or in assembly/machine language. As used herein, the term "machine-readable medium" can refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" can refer to any signal used to provide machine instructions and/or data to a programmable processor.

Some embodiments may be implemented in a computing system that can include a back-end component (e.g., as a data server), or that can include a middleware component (e.g., an application server), or that can include a front-end component (e.g., a client computer having a graphical user interface or a Web browser through which a user may), or any combination of such back-end, middleware, or front-end components. The components of the system may be interconnected by any form or medium of digital data communication (e.g., a communication network). Examples of communication networks can include a local area network ("LAN"), a wide area network ("WAN"), and the Internet.

The computing system may include clients and servers. A client and server can generally be remote from each other and can typically interact through a communication network. The relationship of client and server can arise by virtue of computer programs running on the respective computers and having a client-server relationship to each other.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A portable therapeutic fluid delivery device for delivering a therapeutic fluid into a body of a patient, the fluid delivery device comprising:
    a first part comprising,
        a driving mechanism,
        a flow detector comprising at least one heating element and at least two temperature sensors, and
        a processor;
    a second part comprising,
        a reservoir,
        an exit port, and
        a delivery tube communicating between the reservoir and the exit port;
    wherein the first part and the second part are designed such that upon pairing of the first part with the second part, the at least one heating element and the at least two temperature sensors touch the delivery tube, and wherein the processor, upon activation of the at least one heating element, determines a flow condition of the therapeutic fluid inside the delivery tube based on signals provided by the at least two temperature sensors.

2. The fluid delivery device according claim 1, wherein the fluid delivery device determines a temperature gradient within the therapeutic fluid and determines the flow condition based on the temperature gradient.

3. The fluid delivery device according to claim 1, wherein the flow condition includes at least one of: air bubbles within the delivery tube, an occlusion within the delivery tube, a leakage within the delivery tube, or combinations thereof.

4. The fluid delivery device according to claim 1, wherein the fluid delivery device alerts the patient to conditions of occlusion, air bubbles, leakage in the delivery tube or combinations thereof.

5. The fluid delivery device according to claim 1, wherein the fluid delivery device is remotely controlled.

6. The fluid delivery device according to claim 1, wherein the fluid delivery device comprises a skin securable drug dispensing unit, the drug dispensing unit comprises the first part and the second part.

7. The fluid delivery device according to claim 6, wherein the drug dispensing unit comprising a blood glucose sensing apparatus.

8. The fluid delivery device according to claim 1, wherein the fluid delivery device comprises a skin securable drug dispensing unit comprising buttons, and wherein the drug dispensing unit is operated manually using the buttons.

9. The fluid delivery device according to claim 1, wherein the fluid delivery device disconnects from and reconnects to a skin adherable cradle unit.

10. The fluid delivery device according to claim 1, wherein the first part or the second part comprises an energy supply.

11. The fluid delivery device according to claim 1, further comprising, a handheld remote control unit comprising an integrated blood glucose monitor.

12. The fluid delivery device according to claim 11, further comprising,
a subcutaneous insertable tip, wherein the subcutaneous insertable tip serves both as therapeutic fluid cannula and sensing probe.

13. The fluid delivery device according to claim 1, wherein the driving mechanism comprises a motor.

14. The fluid delivery device according to claim 13, further comprising, a pulse generator coupled to the motor to operate the motor, wherein the fluid delivery device detects an occlusion by detecting a mismatch between pulses supplied to the motor and motor operation.

15. The fluid delivery device according to claim 1, wherein the fluid delivery device delivers power to the at least one heating element, suspends power delivery to the at least one heating element, and delivers power to the motor to begin motor operation subsequent to the suspension of power delivery to the at least one heating element, wherein the power delivered to the motor causes heated therapeutic fluid to flow into the delivery tube.

16. The fluid delivery device according to claim 1, further comprising,
a capacitor, and
a power supply, wherein the fluid delivery device periodically charges the capacitor via the power supply and periodically discharges the capacitor by operating the motor.

17. The fluid delivery device according to claim 16, wherein the fluid delivery device periodically discharges the capacitor by powering the at least one heating element.

18. The fluid delivery device according to claim 16, wherein the delivery device sequentially discharges the capacitor by powering the at least one heating element and operating a motor and recharges the capacitor between operating the motor and powering the at least one heating element.

19. The fluid delivery device according to claim 1, further comprising, a revolution counter;
wherein the processor is coupled to a motor and generates and provides pulses to the motor for powering the motor, and wherein the fluid delivery device detects an occlusion if the flow detector determines a condition of no flow in the delivery tube and there is a mismatch between pulses generated by the processor and a predicted number of motor revolutions.

20. The fluid delivery device according to claim 19, wherein the delivery device, upon sequential operations of the motor and the flow detector, detects air bubbles within the delivery tube and/or an occlusion in the delivery tube.

21. The fluid delivery device according to claim 1, wherein the at least one heating element is proximate to the delivery tube at a first location, wherein the at least one heating element is arranged to directly heat the delivery tube to cause heating of the therapeutic fluid in the delivery tube and a first upstream temperature sensor is placed upstream of the first location and a second downstream temperature sensor is placed downstream of the first location.

22. The fluid delivery device according to claim 21, wherein the fluid delivery device determines the flow condition of the therapeutic fluid within the delivery tube based, at least in part, on temperature measurements performed by the upstream temperature sensor and the downstream temperature sensor.

23. The fluid delivery device according to claim 22, wherein the flow detector further comprises an alignment rack holding the at least one heating element, the at least one upstream temperature sensor, and the at least one downstream temperature sensor; and wherein the alignment rack aligns the heating element, the at least one upstream temperature sensor, and the at least one downstream temperature sensor with the delivery tube.

24. The fluid delivery device according to claim 1, wherein the delivery tube is elastic or flexible.

25. The fluid delivery device according to claim 1, wherein the delivery device, in response to a determination that there is no fluid flow, identifies one or more of several possible problems causing the condition of no fluid flow, the several possible problems comprise a missing pulse of motor operation, a reservoir of the therapeutic fluid being empty, presence of air bubbles in the delivery tube, occlusion occurring in the delivery tube and combinations thereof.

26. The fluid delivery device according to claim 1, wherein the delivery device adjusts or controls delivery of the therapeutic fluid through the delivery tube based, at least in part, on the determined flow rate such that the therapeutic fluid is delivered at a pre-determined delivery rate.

* * * * *